(12) United States Patent
Lin et al.

(10) Patent No.: US 11,530,230 B2
(45) Date of Patent: Dec. 20, 2022

(54) COMPOUND OF 3,3,3',3'-TETRAMETHYL-1,1'-SPIROBIINDANE-BASED PHOSPHINE LIGAND, AND PREPARATION METHOD THEREOF

(71) Applicant: ZHEJIANG UNIVERSITY, Hangzhou (CN)

(72) Inventors: Xufeng Lin, Hangzhou (CN); Linxi Yao, Hangzhou (CN); Shirui Chang, Hangzhou (CN); Lei Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 209 days.

(21) Appl. No.: 16/770,956

(22) PCT Filed: Dec. 14, 2017

(86) PCT No.: PCT/CN2017/116105
§ 371 (c)(1),
(2) Date: Jun. 9, 2020

(87) PCT Pub. No.: WO2019/113874
PCT Pub. Date: Jun. 20, 2019

(65) Prior Publication Data
US 2021/0163514 A1 Jun. 3, 2021

(30) Foreign Application Priority Data
Dec. 13, 2017 (CN) .......................... 201711330428.2

(51) Int. Cl.
*C07F 9/50* (2006.01)
*B01J 31/24* (2006.01)
(Continued)

(52) U.S. Cl.
CPC ........... *C07F 9/5068* (2013.01); *B01J 31/249* (2013.01); *C07C 17/06* (2013.01); *C07C 23/18* (2013.01);
(Continued)

(58) Field of Classification Search
None
See application file for complete search history.

(56) References Cited

U.S. PATENT DOCUMENTS

| 4,626,361 A | 12/1986 | Molaire |
| 5,139,931 A | 8/1992 | Seto et al. |
| 5,516,944 A | 5/1996 | Hoffmann |

FOREIGN PATENT DOCUMENTS

| CN | 1175600 A | 3/1998 |
| CN | 1439643 A | 9/2003 |

OTHER PUBLICATIONS

International Search Report (PCT/CN2017/116105); dated Sep. 3, 2018.

*Primary Examiner* — Joseph R Kosack
(74) *Attorney, Agent, or Firm* — W&G Law Group

(57) ABSTRACT

The present application discloses a 3,3,3',3'-tetramethyl-1,1'-spirobiindane-based phosphine ligand, an intermediate, a preparation method and uses thereof. The compound of phosphine ligand is a compound having a structure represented by formula I or formula II, or an enantiomer, a raceme, or diastereomer thereof. The phosphine ligand can be prepared via a preparation scheme in which the cheap and easily available 6,6'-dihydroxyl-3,3,3',3'-tetramethyl-1,1'-spirobiindane is used as a raw material and the compound represented by formula III serves as the key intermediate. The new phosphine ligand developed by the present application can be used in catalytic organic reaction, in particular as a chiral phosphine ligand that is widely used in many asymmetric catalytic reactions including asymmetric hydrogenation and asymmetric allyl alkylation, and thus it has economic practicability and industrial application prospect.

(Continued)

-continued
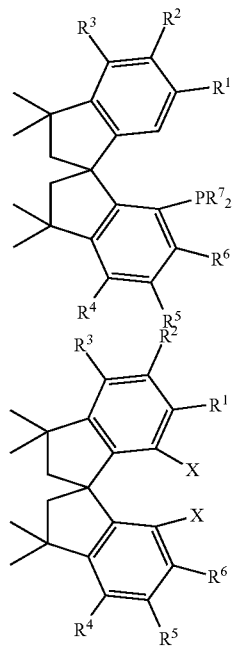
(51) Int. Cl.
  C07C 17/06 (2006.01)
  C07C 23/18 (2006.01)
  C07C 25/22 (2006.01)
  C07C 37/62 (2006.01)
  C07C 39/17 (2006.01)
  C07C 39/42 (2006.01)
  C07C 41/09 (2006.01)
  C07C 43/247 (2006.01)
  C07F 15/00 (2006.01)
(52) U.S. Cl.
  CPC .............. *C07C 25/22* (2013.01); *C07C 37/62* (2013.01); *C07C 39/17* (2013.01); *C07C 39/42* (2013.01); *C07C 41/09* (2013.01); *C07C 43/247* (2013.01); *C07F 9/5022* (2013.01); *C07F 9/5027* (2013.01); *C07F 15/0053* (2013.01); *C07F 15/0066* (2013.01); *B01J 2531/16* (2013.01); *B01J 2531/821* (2013.01); *B01J 2531/824* (2013.01); *C07C 2603/97* (2017.05)
3 Claims, 2 Drawing Sheets

COMPOUND OF 3,3,3',3'-TETRAMETHYL-1,1'-SPIROBIINDANE-BASED PHOSPHINE LIGAND, AND PREPARATION METHOD THEREOF

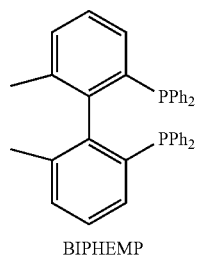
BIPHEMP

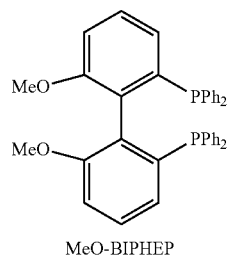
MeO-BIPHEP

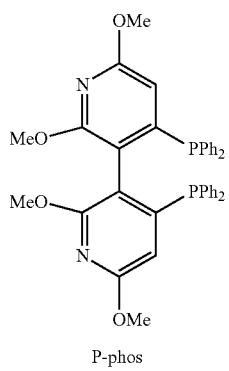
P-phos

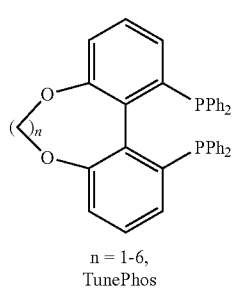
n = 1-6,
TunePhos

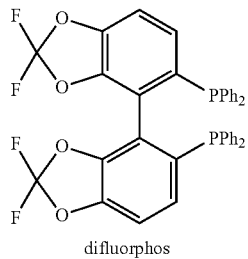
difluorphos

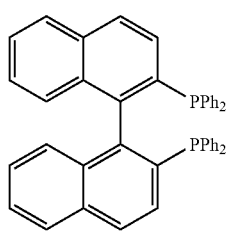

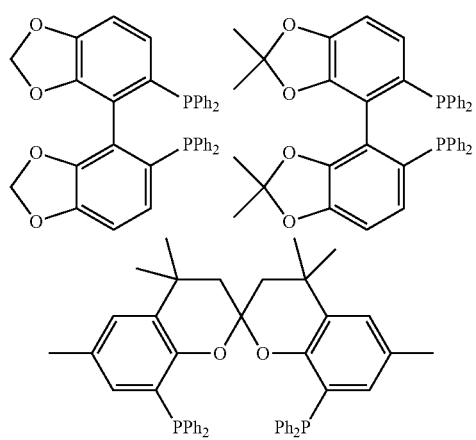

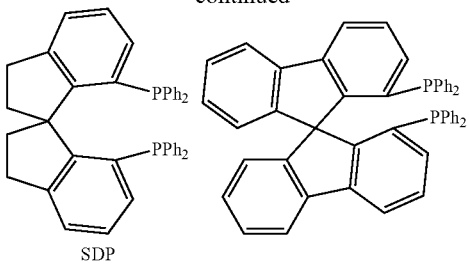
SDP

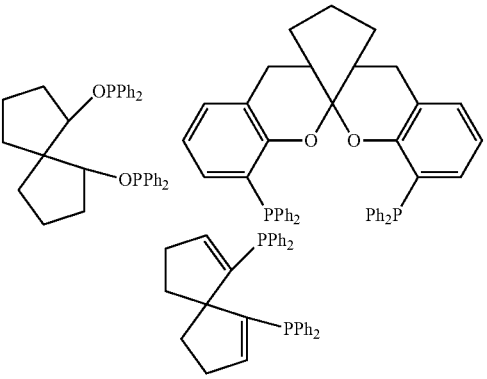

The synthesis design of chiral ligands (for improving catalytic activity and stereoselectivity) follows certain rules, mainly considering electrical and structural factors such as dihedral angle, steric hindrance and skeleton rigidity, etc. It is currently believed that the dihedral angle has a significant influence on the stereoselectivity of asymmetric catalysis (*Acc. Chem. Res.* 2007, 40, 1385-1393, [FIG. 2]; *Tetrahedron: Asymmetry* 15 (2004) 2185-2188; EP1002801; U.S. Pat. No. 6,333,291; *J. Org. Chem.* 1999, 65, 6223; CN 133187dt9 C; *J. Org. Chem.* 2000, 65, 6223; J. AM. CHEM. SOC. 2006, 128, 5955). In addition, bisphosphine ligands containing electron-withdrawing substituents often greatly improve the reaction yield, or improve the enantioselectivity, or change the regioselectivity of the reaction or provide the opposite ring-closed stereoselectivity (*J. Am. Chem. Soc.*, 2009, 131 (28), pp 9604; *Adv. Synth. Catal.* 2017, 359, 2762; *Angew. Chem. Int. Ed.* 2017, 56, 9541; *Chemistry—A European Journal* (2015), 21(12), 4561).

In 1999, Birman et al. synthesized and obtained racemic 1,1'-spirobiindane-7,7'-diol SPINOL from m-methoxybenzaldehyde via a six-step reaction, and obtained the corresponding optical enantiomer through chemical resolution (*Tetrahedron: Asymmetry* 1999, 10, 12), and it indicated that the compound may be used to synthesize various chiral ligands However, according to such a scheme or other published methods, it is obviously impossible to obtain the corresponding 3,3,3',3'-tetramethyl-1,1'-spirobiindane-7,7'-diol. In 2003, using the optically active 1,1'-spirobiindane-7,7'-diol SPINOL as raw material, Zhou Qilin et al. synthesized a 1,1'-spirobiindane-based bisphosphine ligand SDP through a five-step reaction, which was successfully used in the asymmetric catalytic hydrogenation (CN1439643). However, according to their synthetic scheme based on a coupling reaction, it is still impossible to obtain a diphosphine ligand in which the phenyl on the phosphorus atom is substituted with an electron-withdrawing group (substitutents such as p-trifluoromethyl and 3,5-bis(trifluoromethyl)) (Nankai University, 2003, page 26 of doctoral dissertation "Researches on scheme design synthesis and application of chiral spiro-diphosphine ligand", XIE Jianhua; *J. AM CHEM SOC.* 2003, 125, 4404-4405); and starting from the industrially available raw material m-methoxybenzaldehyde, the corresponding 1,1'-spirobiindane-based chiral disphosphine ligand SDP was obtained through at least 11 steps of synthesis reaction and 1 step of chiral resolution, which has lengthy reaction steps, increased costs, and significantly reduced practicability.

It was reported in 1962 that 6,6'-dihydroxyl-3,3,3',3'-tetramethyl-1,1'-spirobiindane (MSPINOL) could be obtained with high yields through acid catalysis directly of from bisphenol series products, and the modified large-scale preparation methods and chiral resolution methods were subsequently reported (referring to the following reaction equation, *J. Chem. Soc.,* 1962, 415-418; *Org. Lett.,* 2004, 6, 2341-2343; US2006/0020150; U.S. Pat. No. 4,879,421; *Bull. Chem. Soc. Japan,* 1977, 44, 496-505):

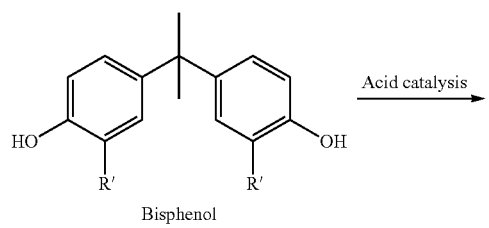

Bisphenol

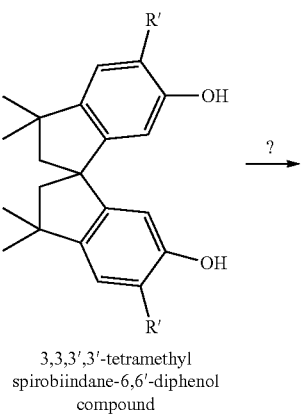

3,3,3',3'-tetramethyl
spirobiindane-6,6'-diphenol
compound

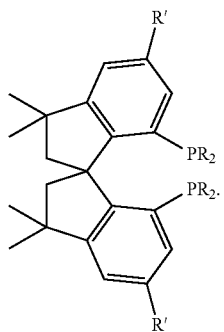

3,3,3',3'-tetramethyl spirobiindane-6,6'-diphenol MSPINOL and its derivatives are known to be mainly used for preparing polymers, but they have not been used for the preparation or application of any ligands. The corresponding raw material, bisphenol, is very cheap and can be prepared by condensation reaction of acetone and phenol or its derivatives. In addition, many industrial bisphenol series products (bisphenol A, bisphenol C, etc.) are available and on large-scale sales, for example, the annually produced and sold bisphenol A in the world are as high as more than 3 million tons, with a price less than 10,000 RMB per ton. The present application is intended to utilize cheap and easily available 3,3,3',3'-tetramethyl spirobiindane-6,6'-diphenol to design and prepare the corresponding 3,3,3',3'-tetramethyl-1,1'-spirobiindane-based phosphine ligand. Compared with 1,1'-spirobiindane-based phosphine ligand such as SDP, such a kind of ligands has no active aryl methylene group on the spiro ring skeleton, the 3,3,3',3'-tetramethyl-1,1'-spirobiindane skeleton is more stable and has stronger rigidity, the raw materials thereof are cheap and abundant, the synthesis scheme is shorter, the preparation cost is low, the practicability is high, and the unique dihedral angle indicates different catalytic effects or uses. Particularly, the phosphine ligands, in which the phenyl group on the phosphorus atom is substituted with an electron-withdrawing group (such as trifluoromethyl, 3,5-bis (trifluoromethyl) and other substituents, can be prepared according to the present application, thereby greatly enriching the phosphine ligand derivatives. Based on the method disclosed in the present application, the 3,3,3',3'-tetramethyl-1,1'-spirobiindane-based phosphine ligand is generally prepared with the industrial large-tonnage raw material bisphenol via a five-step synthesis reaction scheme:

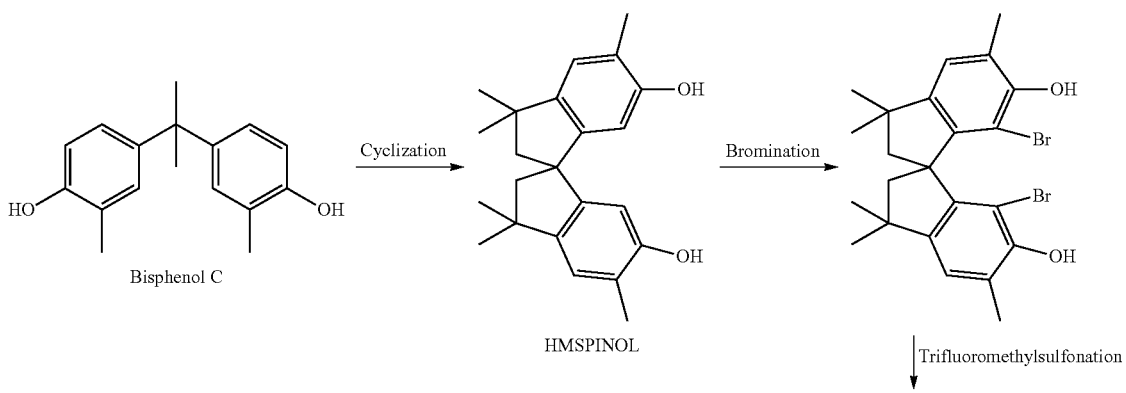

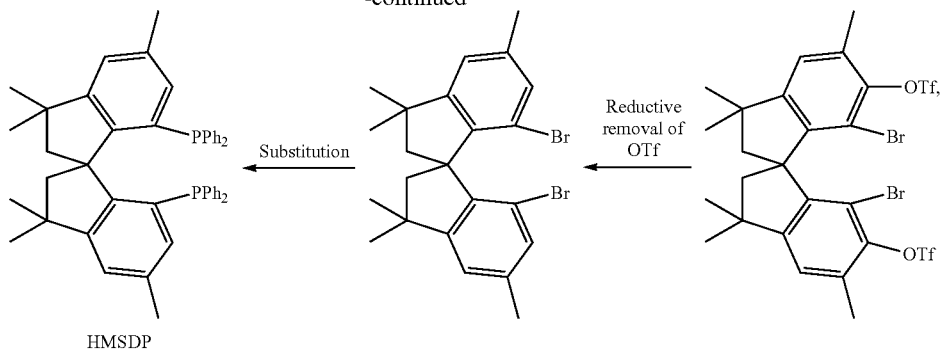
prepared via a seven-step synthesis reaction scheme:
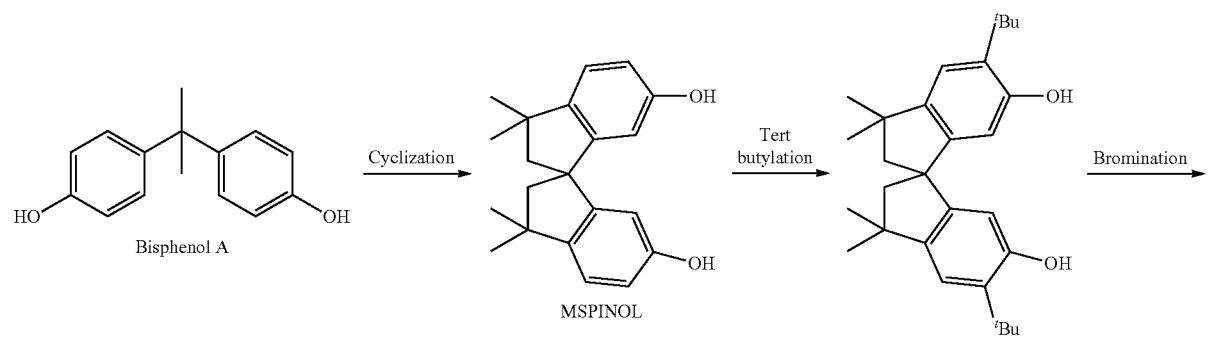
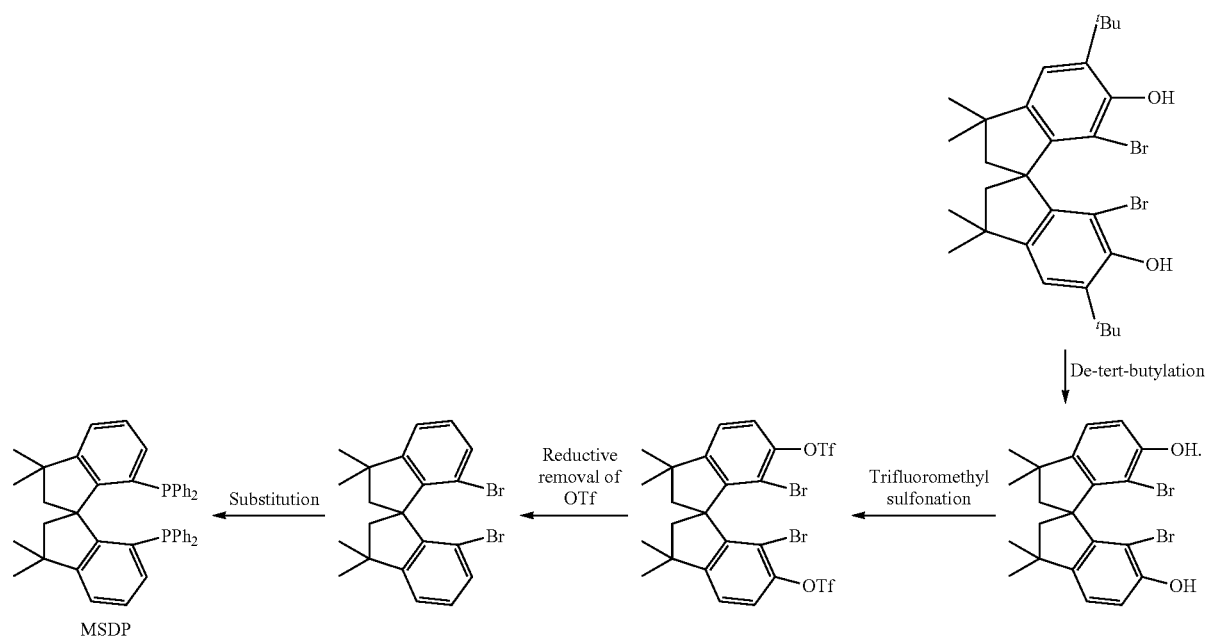

SUMMARY

The present application provides a compound of 3,3,3',3'-tetramethyl-1,1'-spirobiindane-based phosphine ligand, an intermediate, a preparation method and a use thereof.

A 3,3,3',3'-tetramethyl-1,1'-spirobiindane-based phosphine ligand is a compound represented by general I or formula II, or is an enantiomer, a raceme or a diastereomer thereof:

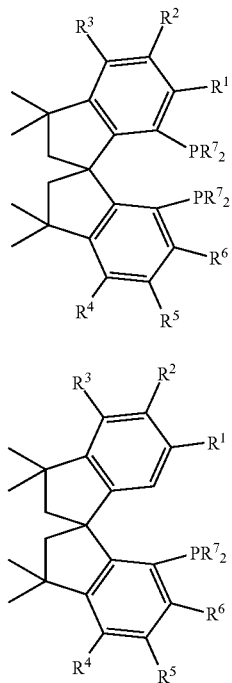

In the formulas: $R^1$ and $R^6$ are each independently selected from the group consisting of hydrogen, $C_1$-$C_{10}$ alkyl or perfluoroalkyl, $C_3$-$C_6$ cycloalkyl, $C_1$-$C_4$ alkoxy or perfluoroalkoxy, aryloxy or substituted aryloxy, heteroaryloxy or substituted heteroaryloxy, aryl or substituted aryl, and heteroaryl or substituted heteroaryl; $R^2$, $R^3$, $R^4$, and $R^5$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, aryloxy or substituted aryloxy, heteroaryloxy or substituted heteroaryloxy, aryl or substituted aryl, and heteroaryl or substituted heteroaryl; and $R^7$ is selected from the group consisting of $C_1$-$C_{10}$ alkyl or perfluoroalkyl, $C_3$-$C_6$ cycloalkyl, $C_6$-$C_{14}$ aryl, substituted aryl, $C_5$-$C_{14}$ heteroaryl, and substituted heteroaryl; and the substituted aryloxy, the substituted aryl or the substituted heteroaryl contains one or more substituents independently selected from the group consisting of halogen, N-dimethylamino, $C_1$-$C_4$ alkyl or perfluoroalkyl, $C_3$-$C_6$ cycloalkyl, $C_1$-$C_4$ alkoxy or perfluoroalkoxy, methylenedioxy, $C_6$-$C_{14}$ aryl, aryloxy, and heteroaryl; and heteroaryl is $C_5$-$C_{14}$ heteroaryl.

An intermediate compound for preparing the 3,3,3',3'-tetramethyl-1,1'-spirobiindane-based phosphine ligand is a compound represented by general formula III, or an enantiomer, a raceme or a diastereomer thereof:

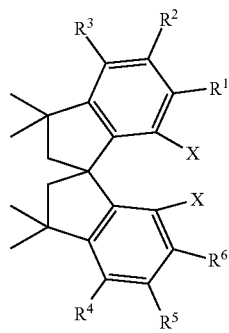

In the formula: $R^1$ and $R^6$ are each independently selected from the group consisting of hydrogen, hydroxyl, $C_1$-$C_{10}$ alkyl or perfluoroalkyl, $C_3$-$C_6$ cycloalkyl, $C_1$-$C_4$ alkoxy or perfluoroalkoxy, aryloxy or substituted aryloxy, heteroaryloxy or substituted heteroaryloxy, aryl or substituted aryl, and heteroaryl or substituted heteroaryl; and $R^2$, $R^3$, $R^4$, and $R^5$ are each independently selected from the group consisting of hydrogen, halogen, $C_1$-$C_{10}$ alkyl or perfluoroalkyl, $C_3$-$C_6$ cycloalkyl, $C_1$-$C_4$ alkoxy or perfluoroalkoxy, aryloxy or substituted aryloxy, heteroaryloxy or substituted heteroaryloxy, aryl or substituted aryl, and heteroaryl or substituted heteroaryl; and the substituted aryloxy, the substituted aryl or the substituted heteroaryl contains one or more substituents independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; the heteroaryl is $C_5$-$C_{14}$ heteroaryl; and X is halogen.

The 3,3,3',3'-tetramethyl-1,1'-spirobiindane-based phosphine ligand represented by formula I is preferably any one of the following compounds:

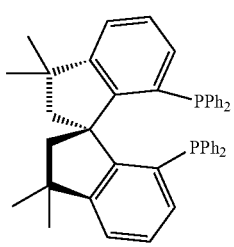

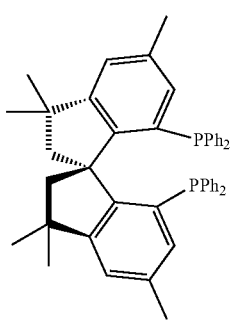

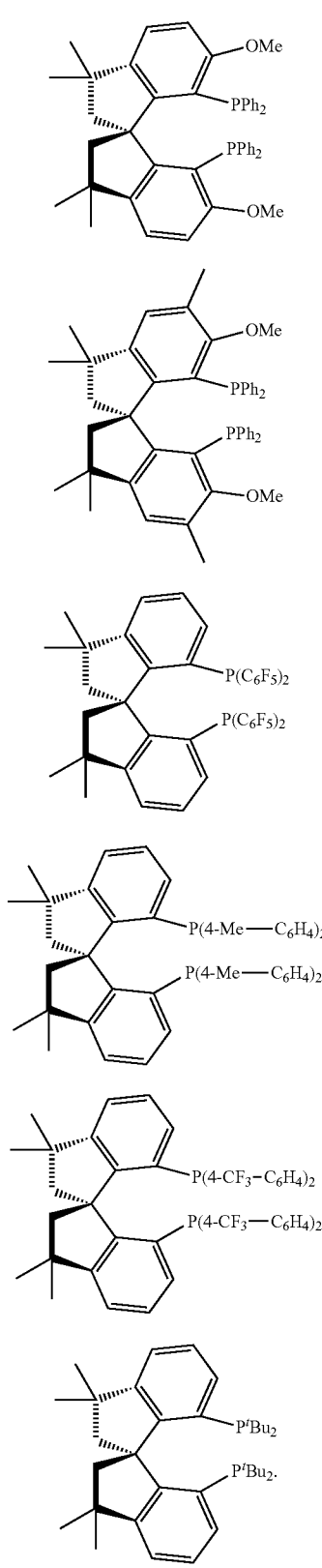
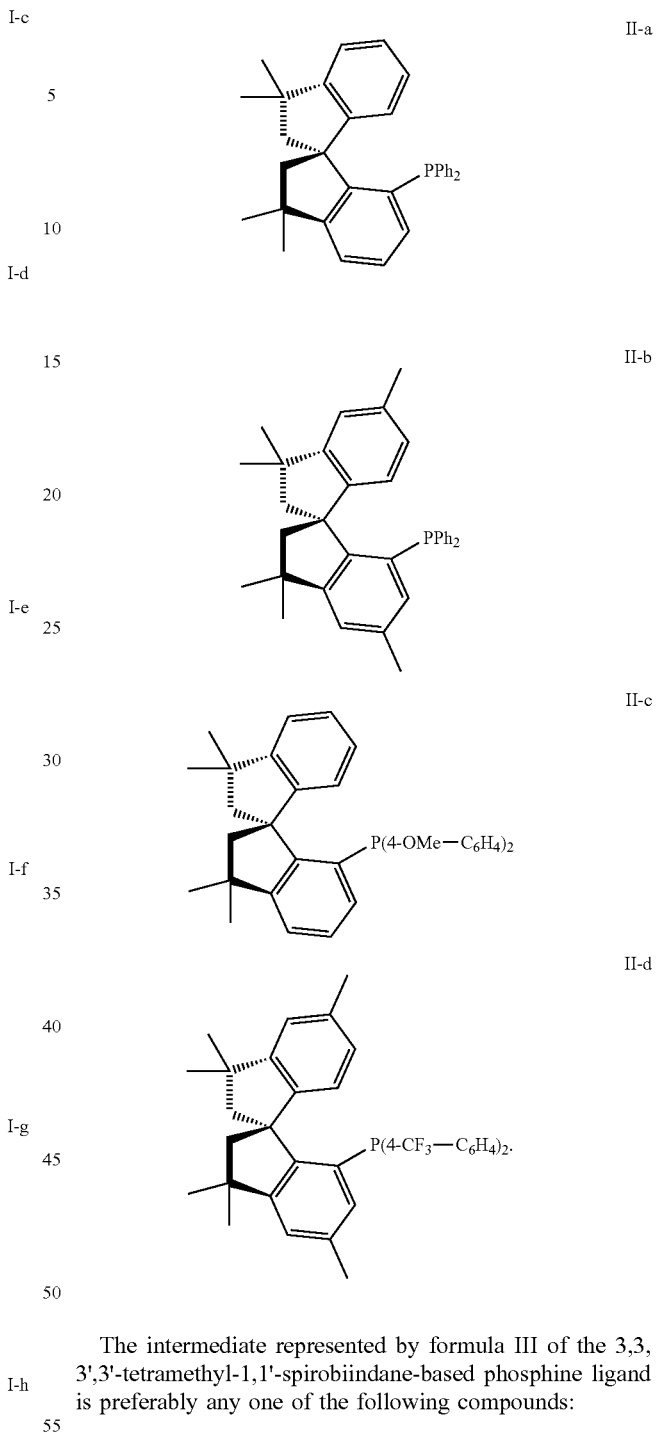
The 3,3,3',3'-tetramethyl-1,1'-spirobiindane-based phosphine ligand represented by formula II is preferably any one of the following compounds:
The intermediate represented by formula III of the 3,3, 3',3'-tetramethyl-1,1'-spirobiindane-based phosphine ligand is preferably any one of the following compounds:
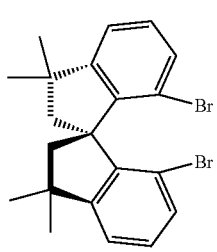

III-b
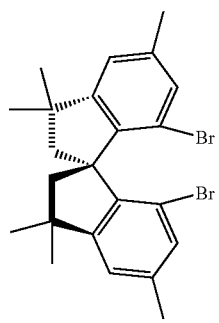
III-c
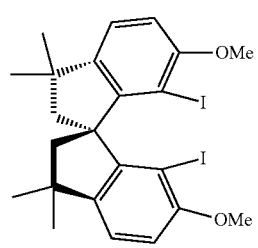
III-d
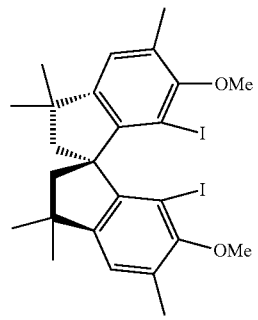
III-e
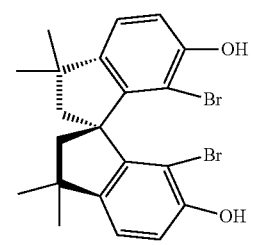
III-f
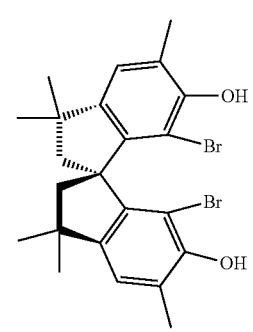
III-g
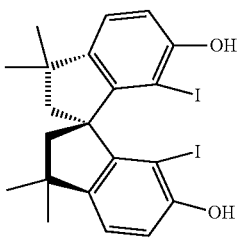
III-h
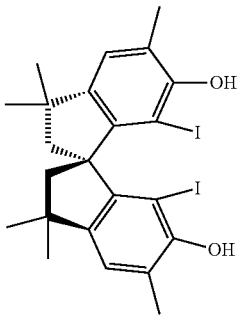
III-i
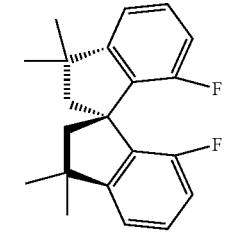
III-j
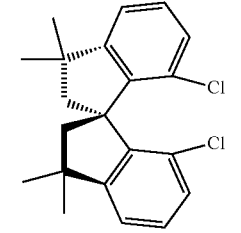
III-k
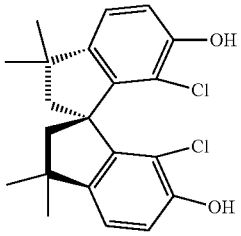
III-l
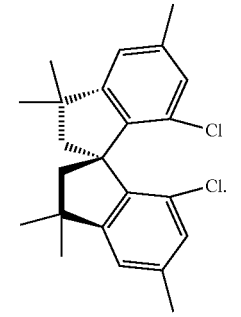

In the compound represented by formula I and the compound represented by formula II, $R^7$ is selected from the group consisting of phenyl, benzyl, pentafluorophenyl, 4-methylphenyl, 4-methoxyphenyl, 4-trifluoromethyl-phenyl, 3,5-dimethylphenyl, 3,5-difluorophenyl, 3,5-dimethoxyphenyl, 3,5-di-tert-butylphenyl, 3,4,5-trimethoxyphenyl, 3,5-dimethyl-4-methoxy-phenyl, 3,5-di-tert-butyl-4-methoxy-phenyl, 3,5-dimethyl-4-methoxy-phenyl, and 3,5-bis(trifluoromethyl)-phenyl.

The intermediate compound represented by formula III can be prepared by using racemic or optically active 6,6'-dihydroxyl-3,3,3',3'-tetramethyl-1,1'-spirobiindane represented by formula 1 as a starting material, through the following reactions: the compound represented by formula 1 (when $R^2$ and $R^5$ are not hydrogen) is first subjected to a halogenation reaction to obtain the compound 2, or the compound represented by formula 1 (when at least one of $R^2$ and $R^5$ is hydrogen) is subjected to tert-butylation, halogenation reaction and de-tert-butylation reaction to obtain the compound 2; the compound 2 is subjected to etherification reaction to prepare and obtain the compound shown as formula III, or the compound 2 is first subjected to esterification using trifluoromethanesulfonic anhydride, and then to palladium-catalyzed coupling reaction or reduction reaction to prepare and obtain the compound shown as formula III;

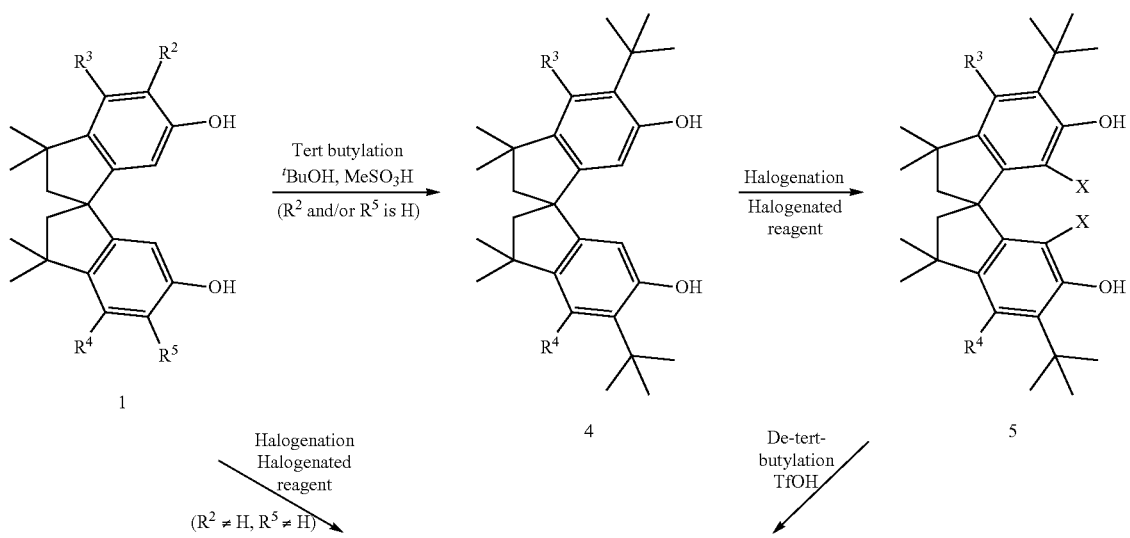

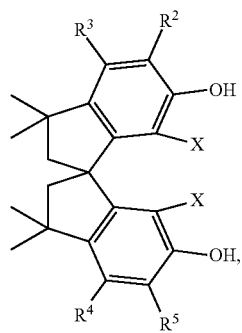

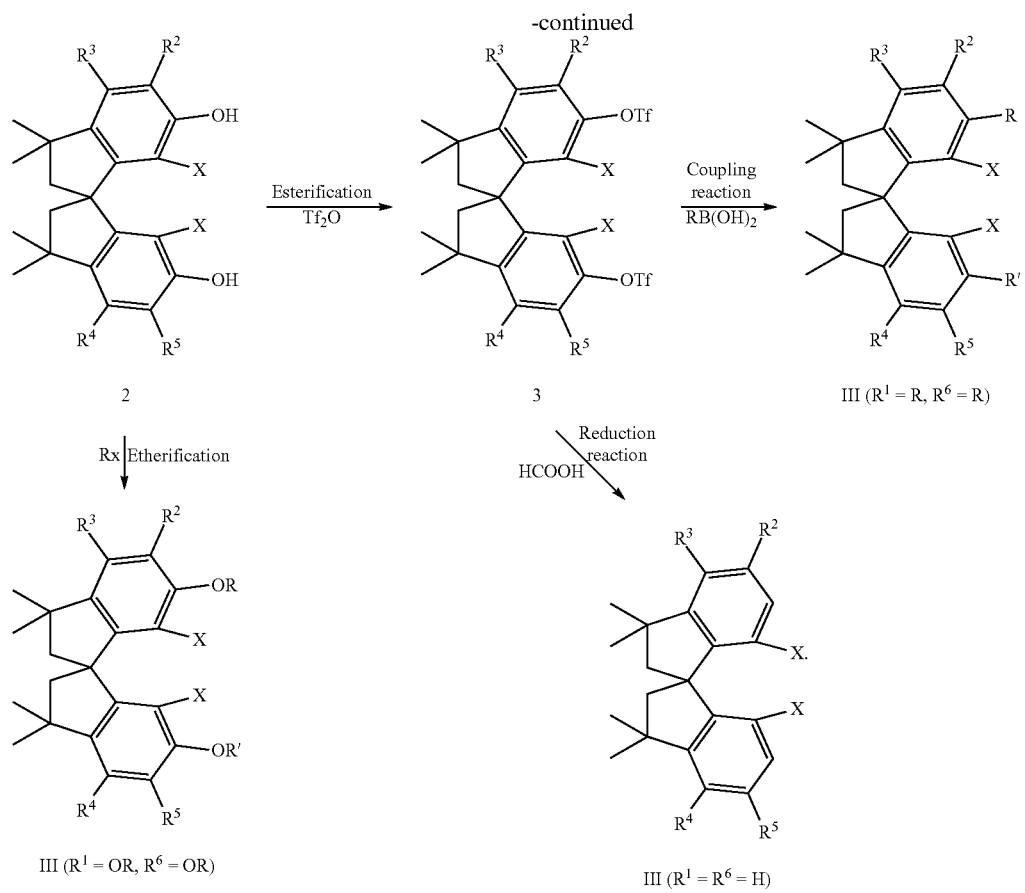

In the formulas 1, 2, 3, 4, and 5, X and $R^1$-$R^6$ are the same as in the formula III, and R is selected from the group consisting of $C_1$-$C_{10}$ alkyl or perfluoroalkyl, $C_3$-$C_6$ cycloalkyl, aryl or substituted aryl, and heteroaryl or substituted heteroaryl. The substituted aryl or the substituted heteroaryl contains one or more substituents independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; and the heteroaryl is $C_5$-$C_{14}$ heteroaryl.

A synthesis method thereof is as follows: when one of $R^2$ and $R^5$ is hydrogen, the step of preparing compound 2 from compound 1 includes the following steps: in dichloromethane or chloroform, in the presence of methanesulfonic acid, the compound 1 reacts with tert-butanol for 2-6 hours at temperature controlled at 0° C. to 40° C., to obtain an intermediate 4; in dichloromethane or ethyl acetate, the intermediate 4 reacts with a halogenated reagent under the catalysis of p-toluenesulfonic acid for 12-24 hours at temperature controlled at 0° C. to 40° C., so as to obtain an intermediate 5; and in toluene or dichloromethane, the intermediate 5 is treated with trifluoromethanesulfonic acid for 1-48 hours to obtain an intermediate 2, in which a molar ratio of the compound 1, the tert-butanol and the methanesulfonic acid is 1:2-4:5-12, a molar ratio of the intermediate 4, the halogenated reagent and the p-toluenesulfonic acid is 1:2-4:0-1, and a molar ratio of the intermediate 5 and the trifluoromethanesulfonic acid is 1:0.8-3;

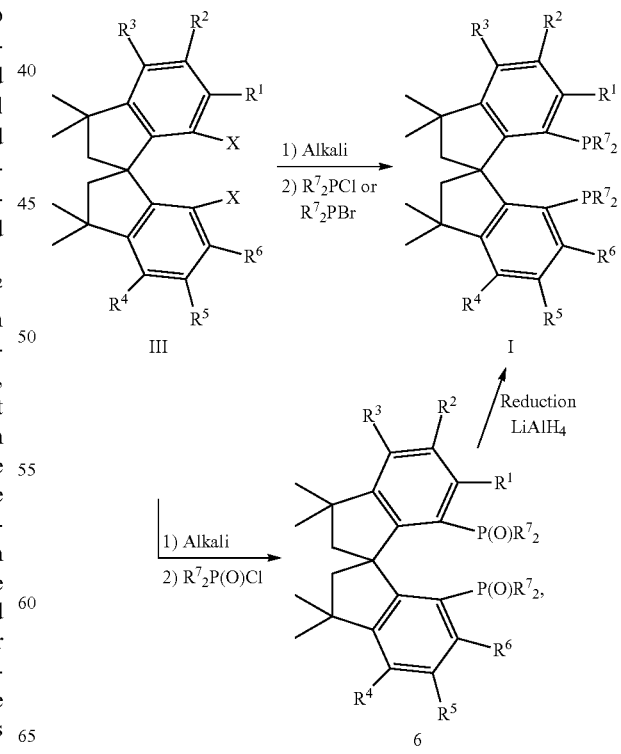

in which, X is halogen, and $R^1$-$R^7$ in formula 6 are the same as in formula I.

Specifically: a reaction method ① includes the following steps: in tetrahydrofuran, while a reaction temperature is controlled at −78° C. to −20° C., the compound of formula III reacts under alkali for 3-5 hours to remove the X group of formula III, and then reacts with $R^7_2$PCl or $R^7_2$PBr at room temperature for 6-12 hours, to obtain the phosphine ligand formula I; or a reaction method ② includes the following steps: in tetrahydrofuran, while the reaction temperature is controlled at −78° C. to −20° C., the compound of formula III reacts under alkali for 3-5 hours to remove the X group of formula III, and then reacts with $R^7_2$P(O)Cl at room temperature for 6-16 hours to obtain the compound 6, and then using ethylene glycol dimethyl ether or tetrahydrofuran as the reaction solvent, the compound 6 is treated with lithium aluminum hydride and methyl trifluoromethylsulfonate 6, and subjected to a reduction reaction at room temperature for 3-6 hours to obtain the phosphine ligand I, in which a molar ratio of the alkali to the compound represented by formula III is 2-10:1, a molar ratio of $R^7_2$PCl or $R^7_2$PBr to the compound represented by formula III is 2-6:1, a molar ratio of $R^7_2$P(O)Cl to the compound represented by formula III is 2-6:1, a molar ratio of lithium aluminum hydride to the compound 6 is 3-10:1, a molar ratio of the methyl trifluoromethansulfonateester to the compound 6 is 1-5:1, and the alkali is tert-butyl lithium, isopropyl magnesium bromide, ethyl magnesium bromide, sec-butyl lithium, or n-butyl lithium.

A synthesis method of compound II is as follows: a racemic or optically active compound represented by formula III, as a raw material, reacts with di-substituted phosphine halide under an effect of an under alkali, and the compound II is prepared through a mono-substitution reaction; or the compound represented by formula III and di-substituted phosphine oxyhalide are subjected to a mono-substitution reaction under an effect of an alkali to prepare a compound represented by formula 7, which is then subjected to a reduction reaction to prepare and obtain the compound II:

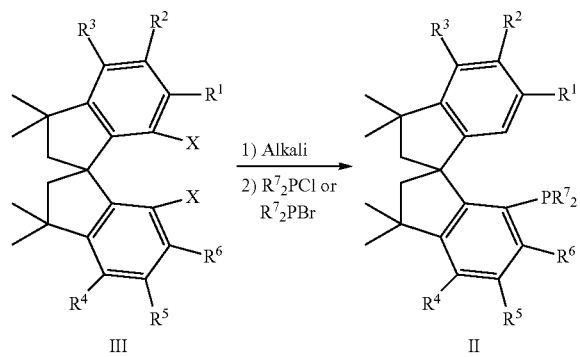

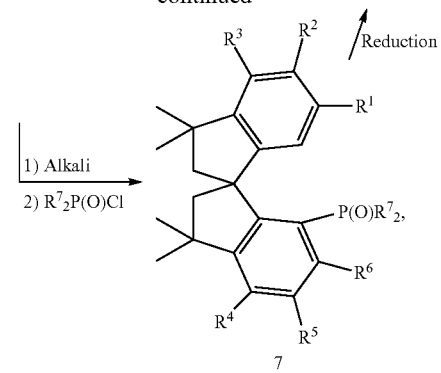

in which, X is halogen, and $R^1$-$R^7$ are the same as in formula II;

Specifically: a reaction method ① includes the following steps: in tetrahydrofuran, while the reaction temperature is controlled at −78° C. to −20° C., the compound III reacts under alkali for 3-5 hours to remove the X group of formula III, and then reacts with $R^7_2$PCl or $R^7_2$PBr at room temperature for 6-12 hours, to obtain the phosphine ligand formula II; or a reaction method ② includes the following steps: in tetrahydrofuran, while the reaction temperature is controlled at −78° C. to −20° C., the compound III reacts under alkali for 3-5 hours to remove the X group of formula III, and then reacts with $R^7_2$P(O)Cl at room temperature for 6-16 hours to obtain compound 7, and then using ethylene glycol dimethyl ether or tetrahydrofuran as the reaction solvent, the compound 6 is treated with lithium aluminum hydride and methyl trifluoromethanesulfonate and subjected to a reduction reaction at room temperature for 3-6 hours to obtain the phosphine ligand II, in which a molar ratio of the alkali to the compound represented by formula III is 2-10:1, a molar ratio of $R^7_2$PCl or $R^7_2$PBr to the compound of formula III is 1-2:1, a molar ratio of $R^7_2$P(O)Cl to the compound represented by formula III is 1-2:1, a molar ratio of the lithium aluminum hydride to the compound 7 is 3-10:1, a molar ratio of the methyl trifluoromethanesulfonate to the compound 7 is 1-3:1, and the alkali is tert-butyl lithium, isopropyl magnesium bromide, ethyl magnesium bromide, sec-butyl lithium, or n-butyl lithium.

DESCRIPTION OF EMBODIMENTS

Figure 1:
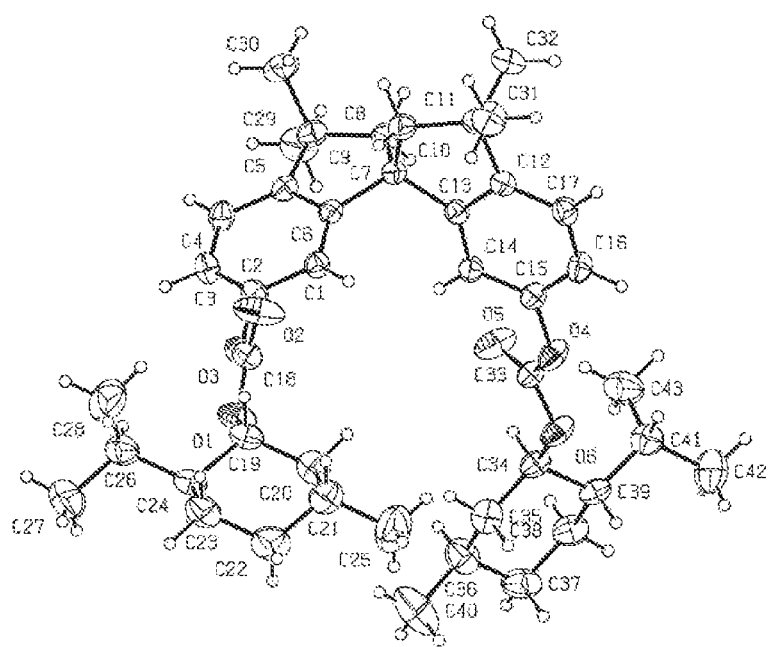
FIG. 1 is an X-ray crystal diffraction pattern of compound RL-MSPINOL in Example 1.
Figure 2:
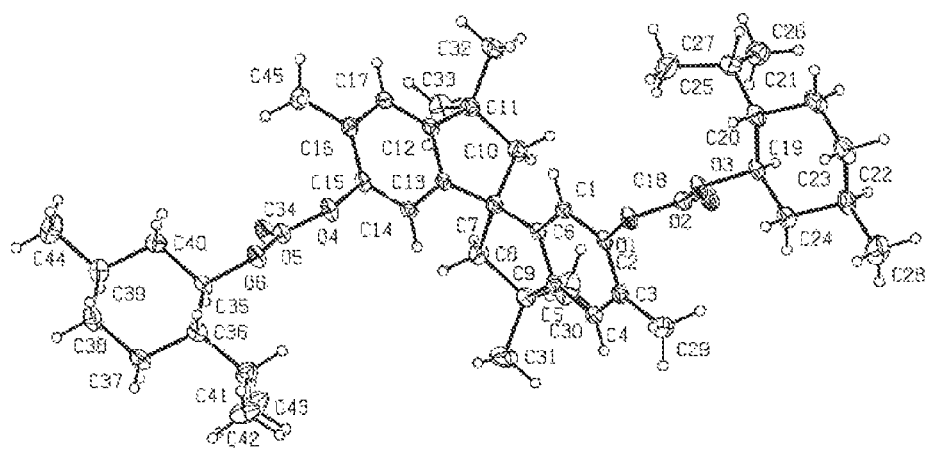
FIG. 2 is an X-ray crystal diffraction pattern of compound SL-HMSPINOL in Example 2.
Figure 3:
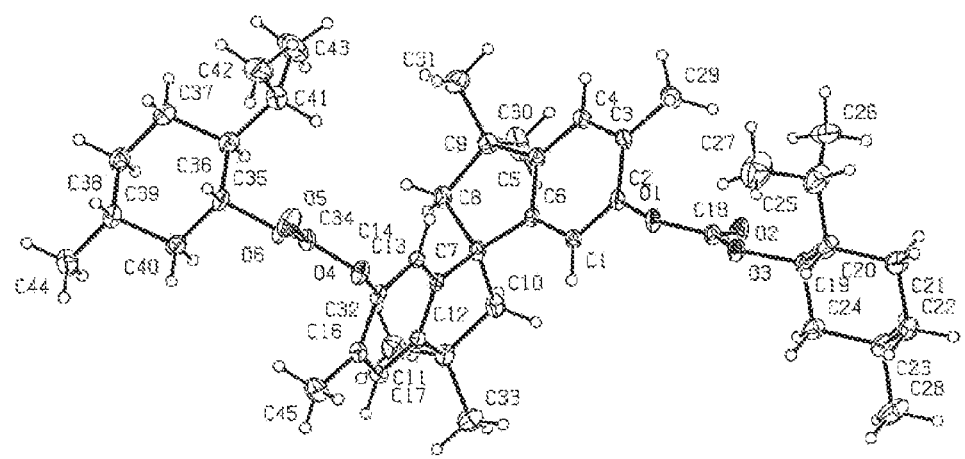
FIG. 3 is an X-ray crystal diffraction pattern of compound RL-HMSPINOL in Example 2.

The following examples are provided to facilitating the understanding of the present application, but are not intended to limit to the present application.

General reaction conditions are described as below: when using air-sensitive reagents, all reactions and controls are performed in a nitrogen-filled glove box or using standard Schlenk technology. The reaction solvents are dried by a general standard process.

Example 1

Synthesis of 3,3,3',3'-tetramethyl-1,1'-spirobiindane-6,6'-diol (MSPINOL)

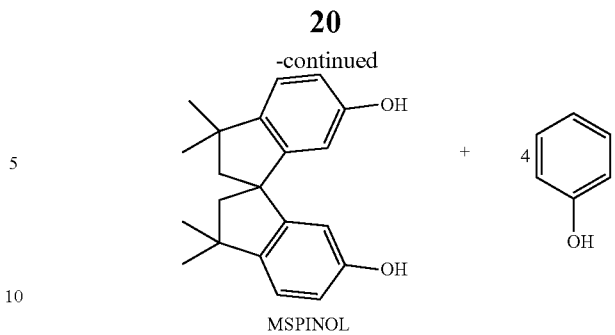

100 g of bisphenol A and 500 mL of methanesulfonic acid were added to a reaction flask, stirred and dissolved to obtain a dark red solution. After reaction under stirring at room temperature for 96 hours, the reaction solution was poured into 600 mL of water, cooled and then filtered with suction, and the obtained solid was washed with water. The solid was dissolved with ethanol under reflux, added with 50° C. warm water until no more solid precipitated, and filtered while being warm, and the filter cake was washed with warm water. After drying, 45 g of white flocculent solid, i.e., 3,3,3',3'-tetramethyl-1,1'-spirobiindane-6,6'-diol (MSPINOL), was obtained, with a yield greater than 99%.

Resolution process of raceme MSPINOL:

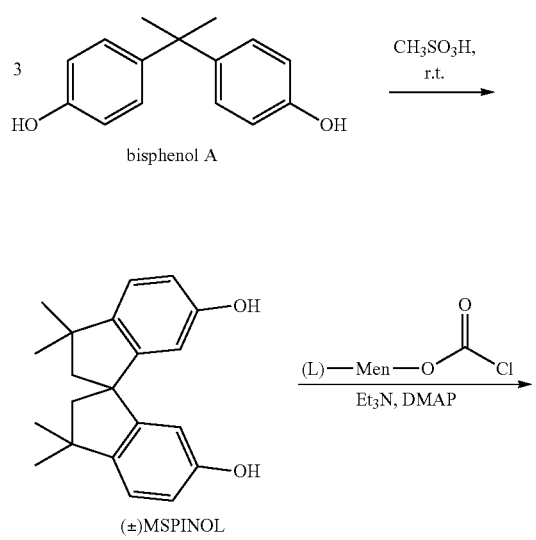

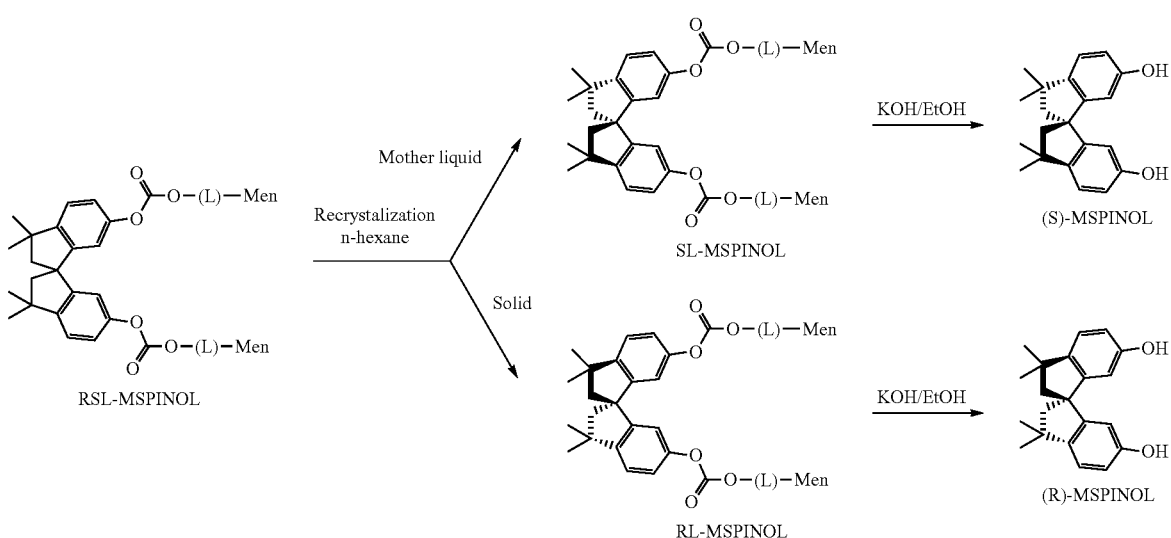

23 g of raceme MSPINOL, 26 ml of triethylamine and 0.22 g of 4-(N, N-dimethylamino) pyridine (DMAP) were dissolved in 200 ml of dichloromethane, cooled in an ice bath and added with 32.6 g of L-menthol chloroformate within 30 minutes. Then, the reaction carried out under stirring at room temperature for 6 hours. TLC confirmed that the reaction was sufficient. Next, the reaction solution was washed with dilute hydrochloric acid and brine successively, the organic phase was dried over anhydrous sodium sulfate and filtered, and the filtrate was concentrated and dried to obtain a pair of diastereomer intermediates (RSL-MSPINOL), which was then recrystallized with n-hexane twice to obtain a single diastereomer (RL-MSPINOL) with a yield of 60%; and a retention time of the compound was 23.5 min (HPLC: C18 column, mobile phase, methanol:water=98:2, flow rate 0.8 mL/min, 254 nm). The crystal mother liquor was recrystallized three times with n-hexane to obtain another diastereomer (SL-MSPINOL) with a yield of 30%, and the retention time of this compound was 25 min (HPLC: C18 column, mobile phase methanol:water=98:2, flow rate 0.8 mL/min, 254 nm). In addition, D-menthol chloroformate may be used instead of L-menthol chloroformate in the above process, and the another diastereomer (SL-MSPINOL) may be obtained with a yield of 55%.

1.5 g of compound RL-HMSPINOL was dissolved in 10 ml of methanol, added with 0.66 g of potassium hydroxide, refluxed for 1 hour, concentrated, then added with 20 ml of dichloromethane, and washed successively with dilute hydrochloric acid and saturated brine, the organic phase was dried over sodium sulfate and suction filtered, the filtrate was concentrated and then subjected to flash column chromatography to obtain (R)-MSPINOL with a yield equal to or greater than 98%. Similarly, SL-MSPINOL was quantitatively obtained in the form of (S)-MSPINOL by hydrolysis in the same process as above.

Single crystal data of compound RL-MSPINOL are as follows (FIG. 1):
Cell: a=9.6816(3) b=10.6124(4) c=39.6866(13)
alpha=90 beta=90 gamma=90; Temperature: 293 K
Volume 4077.6(2); Space group P 21 21 21; Hall group P 2ac 2ab Example 2

Synthesis of 3,3,5,3',3',5'-hexamethyl-1,1'-spirobiindane-6,6'-diol (HMSPINOL)

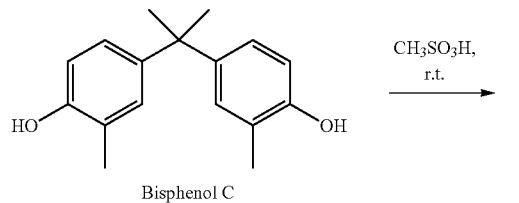

Bisphenol C

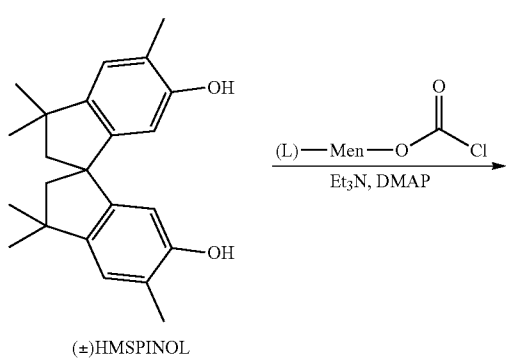

(±)HMSPINOL

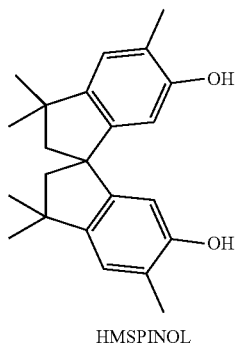

HMSPINOL 50 g of bisphenol C and 250 mL of methanesulfonic acid were added to a 500 mL round-bottom flask. After reaction while stirring at room temperature for 3 days, 100 mL of methanesulfonic acid was additionally added, and the reaction continued for 1 day to stop the reaction. The reaction solution was poured into a beaker containing 300 mL of crushed ice, and filtered with suction, and the filter cake was washed successively with saturated sodium bicarbonate solution and water. After washing, the obtained crude product was transferred to a 500 mL single-necked flask, an appropriate amount of ethanol was added to just dissolve the product at reflux temperature, water was added until a solid was apparently precipitated, the mixture was fully stirred and cooled to precipitate a large amount of solids, then suction filtered and washed, and the filter cake was dried to obtain 20 g white powdery solid, 3,3,5,3',3',5'-hexamethyl-1,1'-spirobiindane-6,6'-diol (HMSPINOL), with a yield of 92%, mp: 250-251° C. ($^1$H NMR (400 MHz, CDCl$_3$): δ=6.92 (s, 2H), 5.85 (s, 2H), 3.95 (s, 2H), 2.30 (d, J=13.0 Hz, 2H), 2.21 (s, 6H), 2.17 (d, J=13.0 Hz, 2H), 1.39 (s, 6H), 1.30 (s, 6H); $^{13}$C NMR (100 MHz, CDCl$_3$): δ=153.18, 150.05, 144.54, 123.55, 122.95, 110.50, 59.40, 57.00, 43.12, 31.88, 30.15, 15.97; HRMS (EI-TOF): calcd for C$_{23}$H$_{28}$O$_2$ 336.2089, found 336.2085.

A resolution process of raceme HMSPINOL:

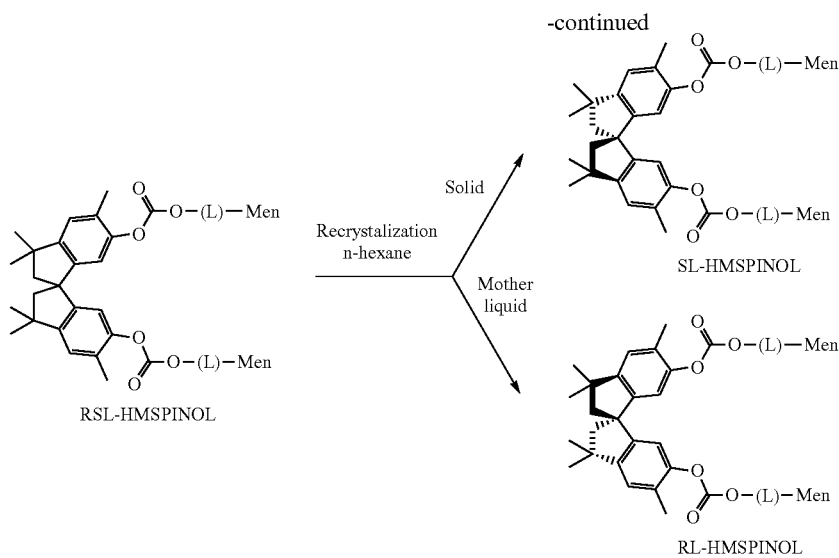
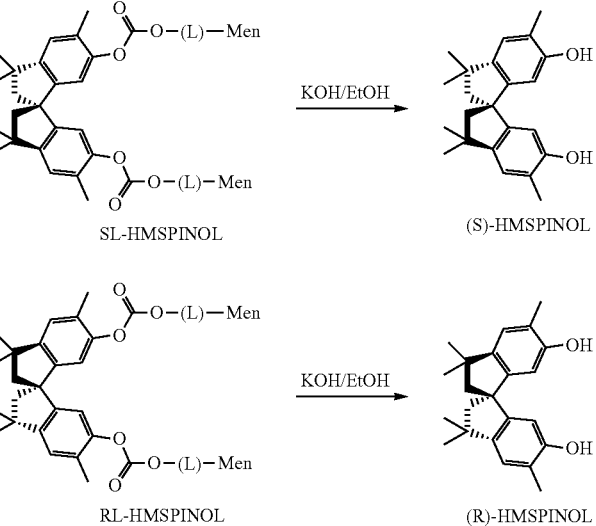

5 g of raceme HMSPINOL, 9.6 mL of triethylamine and 0.18 g of 4-(N, N-dimethylamino) pyridine (DMAP) were dissolved in 50 mL of dichloromethane, and 7.3 mL of L-menthol chloroformate was added within 30 minutes. Then, the reaction carried out under stirring at room temperature for 3 hours. TLC confirmed that the reaction was sufficient. Next, the reaction solution was washed with dilute hydrochloric acid and brine successively, the organic phase was dried over anhydrous sodium sulfate and filtered, and the filtrate was concentrated to dryness to obtain a pair of diastereomer intermediates (RSL-HMSPINOL), which was then recrystallized with n-hexane. 10 mL of n-hexane was added to the residue of the concentrated solution, dissolved by stirring, then cooled to −20° C. and kept at −20° C. for 12 hours to precipitate a solid, and suction filtered (the filtrate was the crystallization mother liquor, which was collected separately for use), and the obtained solid was washed with cold n-hexane. The above recrystallization process was repeated twice, so that a single diastereomer (SL-HMSPINOL) with a yield of 50% could be obtained; the retention time of the compound was 28.02 min (HPLC: C18 column, 100% MeOH mobile phase, flow rate 1.0 mL/min, 254 nm). The above-mentioned separately collected crystallization mother liquor was concentrated to dryness and then added with 13 mL of n-hexane, cooled to −4° C. and crystallized under heat preservation for 48 hours to precipitate a solid, suction filtered and washed with cold n-hexane to obtain another single diastereomer (RL-HMSPINOL) with a yield of 35%; and the retention time of this compound was 24.67 min (HPLC: C18 column, 100% MeOH mobile phase, flow rate 1.0 mL/min, 254 nm).

1.5 g of compound SL-HMSPINOL was dissolved in 20 mL of ethanol, added with 0.66 g of potassium hydroxide, refluxed for 2 hours, concentrated, then added with 20 mL of dichloromethane, and washed successively with dilute hydrochloric acid and saturated brine. The organic phase was dried over sodium sulfate and suction filtered, the filtrate was concentrated and then subjected to flash column chromatography to obtain (S)-HMSPINOL with a yield of 98% or greater. Similarly, RL-HMSPINOL was quantitatively obtained in the form of (R)-HMSPINOL by hydrolysis in the same process as above.

Synthesis of (R)-3,3,3',3'-tetramethyl-7,7'-dibromo-1,1'-spirobiindane ((R)-III-a)

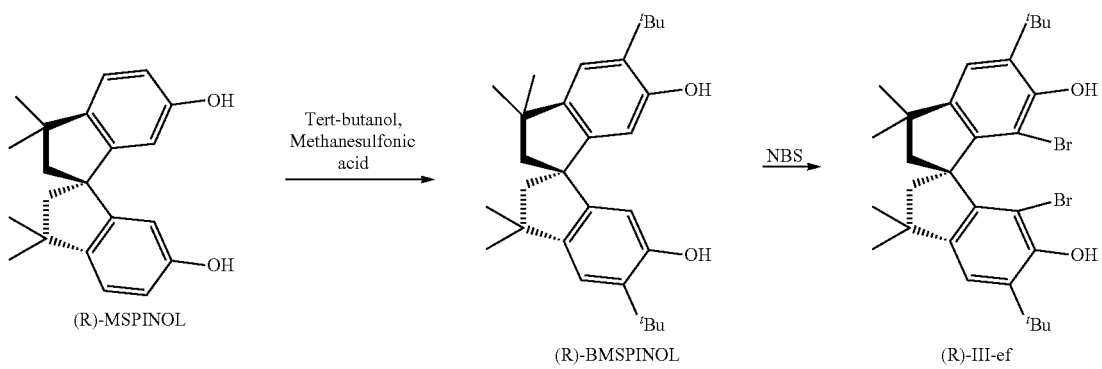

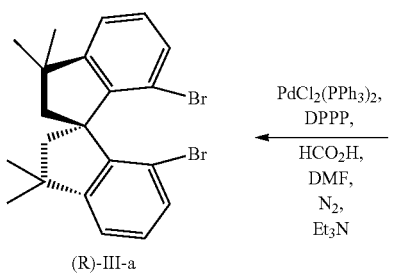 (R)-III-a

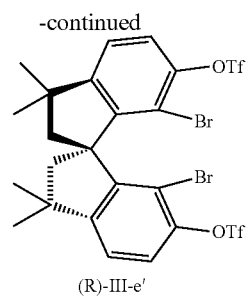 (R)-III-e'

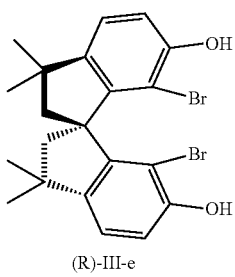 (R)-III-e 15.4 g of compound (R)-MSPINOL (molecular weight: 308, 0.05 mol), 15 mL of tert-butanol (0.156 mol), and 180 mL of dichloromethane were added in a reaction flask. After stirring evenly (suspension), 27 mL of methanesulfonic acid (0.41 mol) was added dropwise under ice-water bath cooling, and the turbidity gradually disappeared; after the dropwise addition finished, the reaction liquid became turbid again when the ice-water bath was removed, and the stirring reaction carried out for another 2 hours, and then was quenched by adding 100 mL of ice water. The reaction solution was distilled to remove dichloromethane under reduced pressure, and then at least 200 mL of ethyl acetate was added under stirring to dissolve all precipitated solids; a liquid separation was performed, the aqueous phase was extracted with ethyl acetate, and the organic phases were combined; the organic phase was washed with saturated brine, dried over anhydrous sodium sulfate, and then was subjected to suction filtering; the filtrate was concentrated to dryness to obtain a white-like solid, which was then purified by rapid ethanol-water recrystallization. The solid was dissolved with an appropriate amount of ethanol at 80° C., until it was just completely dissolved under the reflux state of ethanol, then added with warm water slowly under stirring to precipitate the solid until no more solid precipitated, suction filtered while being still warm, and fully washed with warm water. The filter cake was dried to obtain 20.2 g of white solid compound (R)-BMSPINOL, with a yield of 96%. $^1$H NMR (400 MHz, CDCl$_3$) δ 7.05 (s, 2H), 5.41 (s, 2H), 3.05 (s, 2H), 2.28 (d, J=13.0 Hz, 2H), 2.10 (d, J=13.0 Hz, 2H), 1.42 (s, 6H), 1.35 (s, 18H), 1.28 (s, 6H).

Example 4

Synthesis of (R)-3,3,5,3',3',5'-hexamethyl-7,7'-dibromo-1,1'-spirobiindane ((R)-III-b)

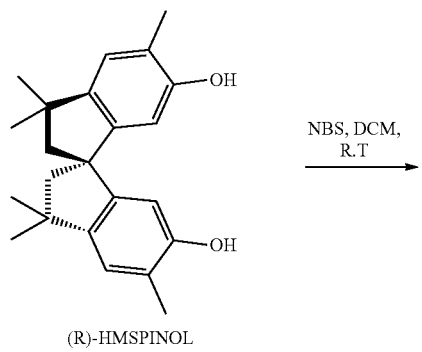 (R)-HMSPINOL

Figure 4:
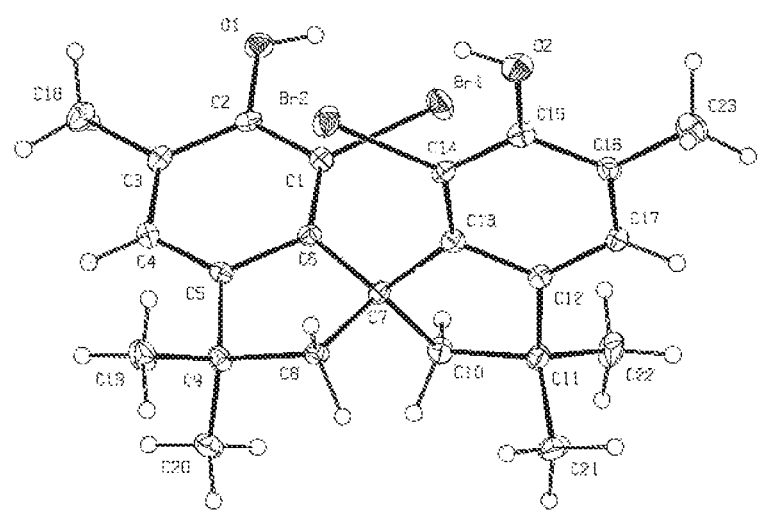
FIG. 4 is an X-ray crystal diffraction pattern of compound (R)-III-f in Example 4.

In a 500 mL three-necked flask, 18 g (R)-HMSPINOL and 200 mL of dichloromethane were added, and 19.8 g of N-bromosuccinimide was added in batches under electromagnetic stirring. The mixture was stirred for 1 hour at room temperature, and TLC (petroleum ether:ethyl acetate=5:1) confirmed that the reaction is finished. A saturated sodium bisulfite solution was added while stirring for 1 hour. The liquid was separated, the aqueous phase was washed with 100 mL of dichloromethane, and the organic phase was combined and washed with saturated brine. The organic phase was dried over anhydrous sodium sulfate and suction filtered. The filtrate was freed from the solvent to obtain 26.4 g of light-yellow solid powder (R)-III-f, with a yield of 99.8%, mp: 228° C. $^1$H NMR (400 MHz, CDCl$_3$) δ=6.88 (s, 2H), 5.57 (s, 2H), 2.47 (d, J=13.1 Hz, 2H), 2.31 (s, 6H), 2.25 (d, J=13.0 Hz, 2H), 1.39 (s, 6H), 1.33 (s, 6H). $^{13}$C NMR (101 MHz, CDCl$_3$) δ=149.25, 145.61, 142.67, 124.51, 123.60, 107.15, 60.85, 55.57, 43.06, 32.58, 29.28, 17.11; HRMS (EI-TOF): calcd for C$_{23}$H$_{26}$Br$_2$O$_2$ 492.0300, found 492.0302;

Single crystal data are as follows (the structure is shown in FIG. 4):
Cell: a=7.5979(5) b=14.0001(10) c=19.6290(12)
alpha=90 beta=90 gamma=90; Temperature: 171 K
Space group P 21 21 21; Hall group P 2ac 2ab

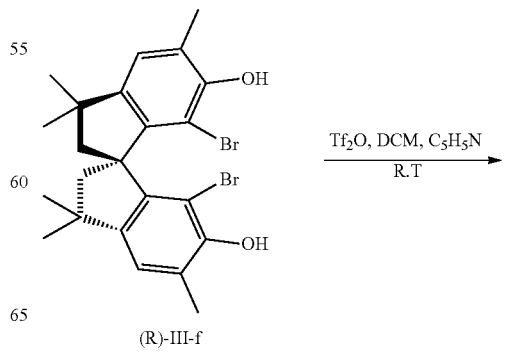 (R)-III-f

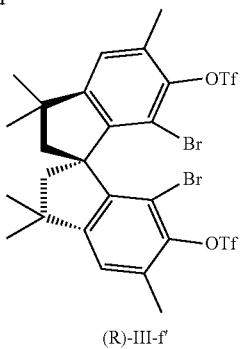

(R)-III-f'

In a three-necked flask, (R)-III-f (9 g, 18.2 mmol) was added under nitrogen protection, dichloromethane (150 mL) and pyridine (7.7 mL) were then added in sequence, and trifluoromethanesulfonic anhydride (7.7 mL) was added slowly under an ice bath. The reaction was conducted while stirring at room temperature for 1 hour, and monitored by TLC until the reaction was completed. The reaction solution was washed successively with dilute hydrochloric acid, saturated sodium bicarbonate solution, and saturated sodium chloride solution. The organic phase was dried over anhydrous sodium sulfate, and suction filtered. The filtrate was concentrated to dryness, and subjected to flash silica gel column chromatography (eluent: petroleum ether:ethyl acetate=10:1), to obtain a white solid powder (R)-III-f' (13.2 g, yield: 96%), mp: 206° C. $^1$H NMR (400 MHz, CDCl$_3$): δ=7.02 (s, 2H), 2.55 (d, J=13.2 Hz, 2H), 2.45 (s, 6H), 2.30 (d, J=13.2 Hz, 2H), 1.42 (s, 6H), 1.36 (s, 6H); $^{19}$F NMR (400 MHz, CDCl$_3$): δ=−72.18 (s); $^{13}$C NMR (100 MHz, CDCl$_3$): δ=153.74, 145.12, 144.55, 132.61, 124.80, 123.33, 120.14, 116.95, 113.77, 113.37, 61.28, 54.92, 43.43, 32.37, 28.81, 18.16; HRMS (EI-TOF): calcd for C$_{25}$H$_{24}$F$_2$Br$_2$O$_2$S$_2$ 755.9285, found 755.9285;

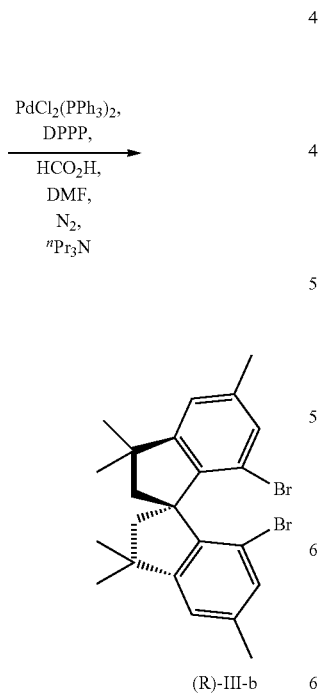

In a three-necked flask, (R)-III-f (12.9 g), bis(triphenylphosphine) palladium chloride (515 mg), and 1,3-bis(diphenylphosphine propane) (361 mg), under nitrogen protection, were added sequentially with N, N-dimethylfonnamide (150 mL, DMF) and tripropylamine (38.5 mL), and formic acid (5.1 mL) was added slowly at 0° C. The reaction was conducted under stirring in an oil bath at 80° C. for 1 hour. After the reaction was completed, the solution was cooled to room temperature, and the reaction was quenched with water. Ethyl acetate was added to perform liquid separation extraction. The aqueous phase was extracted with ethyl acetate again. The organic phase was combined, then washed with 30% hydrogen peroxide solution for 5 minutes, then washed successively with 4 mol/L HCl solution, saturated sodium bicarbonate solution and saturated sodium chloride solution, dried over anhydrous sodium sulfate, and subjected to suction filtering. The filtrate was concentrated to dryness, and then subjected to silica gel column flash column chromatography (eluent: petroleum ether:ethyl acetate=50:1) to obtain white powdery solid (R)-III-b, with a yield of 95%, mp: 202° C. $^1$H NMR (400 MHz, CDCl$_3$): δ=7.18 (s, J=7.4 Hz, 2H), 6.97 (s, 2H), 2.57 (d, J=13.1 Hz, 2H), 2.38 (s, 6H), 2.28 (d, J=13.1 Hz, 2H), 1.43 (s, 6H), 1.38 (s, J=8.2 Hz, 6H); $^{13}$C NMR (100 MHz, CDCl$_3$): δ=154.92, 142.48, 138.92, 131.88, 122.32, 119.14, 59.79, 55.36, 43.42, 32.56, 28.94, 20.98.

Example 5

Synthesis of 3,3,3',3'-tetramethyl-5,5'-di-tert-butyl-7,7'-diiodo-1,1'-spirobiindane-6,6'-diol (III-bg)

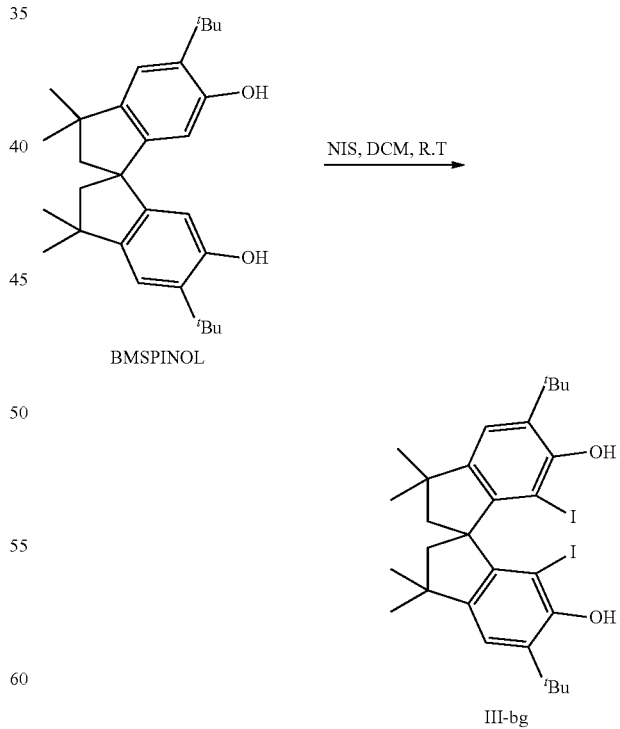

In a reaction flask, 1.5 g of HMSPINOL, 0.15 g of p-toluenesulfonic acid, and 45 mL of dichloromethane were added, and 2.1 g of N-iodosuccinimide was added slowly under magnetic stirring. The mixture reacted under stirring at room temperature for 6 hours, and TLC (petroleum ether:ethyl acetate=5:1) confirmed the end of the reaction. Excessive saturated sodium disulfite solution was added, and the stirring was continued for 1 hour. The liquid was separated, and the aqueous phase was washed with 20 mL of dichloromethane. The organic phase was combined, washed with saturated brine, dried over anhydrous sodium sulfate, and suction filtered. The filtrate was freed from the solvent to obtain 2.24 g of solid powder III-bg. $^1$H NMR (400 MHz, CDCl$_3$) δ 7.01 (s, 2H), 5.68 (s, 2H), 2.45 (d, J=13.1 Hz, 2H), 2.25 (d, J=13.1 Hz, 2H), 1.42 (s, 6H), 1.41 (s, 18H), 1.33 (s, 6H).

Example 6

Synthesis of 3,3,5,3',3',5'-hexamethyl-7,7'-diiodo-1, 1'-spirobiindane-6,6'-diol (III-h)

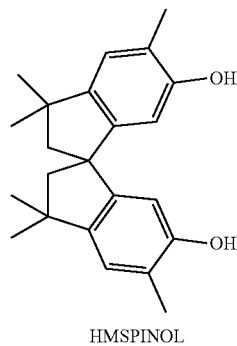

HMSPINOL

NIS, DCM, R.T
→

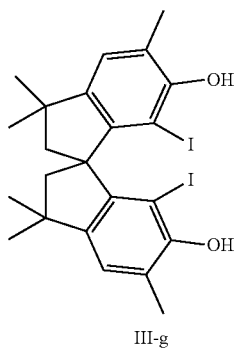

III-g

In a reaction flask, 1.5 g of HMSPINOL, 0.195 g of p-toluenesulfonic acid, 45 mL of dichloromethane were added, and 2.254 g of N-iodosuccinimide was added slowly under magnetic stirring. The mixture was stirred at room temperature for 5 hours until TLC (petroleum ether:ethyl acetate=5:1) confirmed the end of the reaction. Excessive saturated sodium bisulfite solution was added, the stirring was continued for 1 hour, and the liquid was separated. The aqueous phase was washed with 20 mL of dichloromethane. The organic phases were combined, washed with saturated brine, dried over anhydrous sodium sulfate, and subjected to suction filtering. The filtrate was freed from the solvent to obtain 2.44 g of yellow solid powder III-h, with a yield of 93%.

Example 7

Synthesis of (R)-3,3, 3',3'-tetramethyl-6,6'-dimethoxy-7,7'-dibromo-1,1'-spirobiindane (III-h)

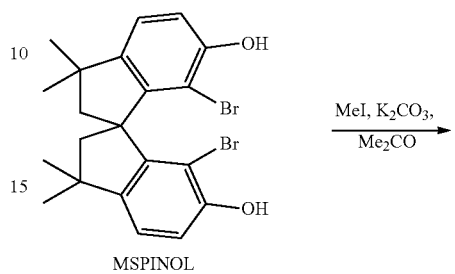

MSPINOL

MeI, K$_2$CO$_3$,
Me$_2$CO
→

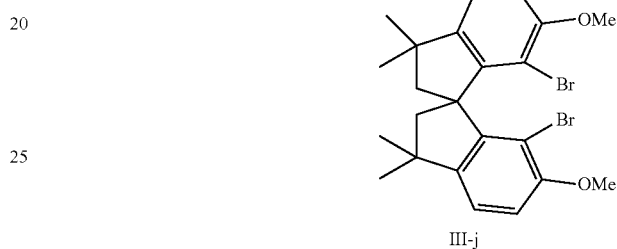

III-j

In a reaction flask, 3 g of MSPINOL and 3.56 g of potassium carbonate were added, 30 mL of acetone was added, and 1.6 mL of methyl iodide was injected. The reaction solution was warmed up to 35° C., and reacted under stirring for 12 hours until TLC monitored that the raw materials disappeared and completely became a product. 60 mL of concentrated ammonia was added while stirring for 2 hours. After being cooled to room temperature, the solution was suction filtered, washed with warm water 3 times, and dried to obtain 3.04 g of white powder III-j, with a yield of 96%. $^1$H NMR (400 MHz, CDCl$_3$) δ 7.08 (dd, J=8.2, 4.4 Hz, 2H), 6.82 (dd, J=8.2, 4.4 Hz, 2H), 3.85 (6H), 2.61 (d, J=13.0 Hz, 2H), 2.27 (d, J=13.0 Hz, 2H), 1.42 (s, 6H), 1.35 (s, 6H).

Example 8

Synthesis of (R)-3,3,5,3',3',5'-hexamethyl-6,6'-diphenyl-7,7'-dibromo-1,1'-spirobiindane ((R)-III-ff)

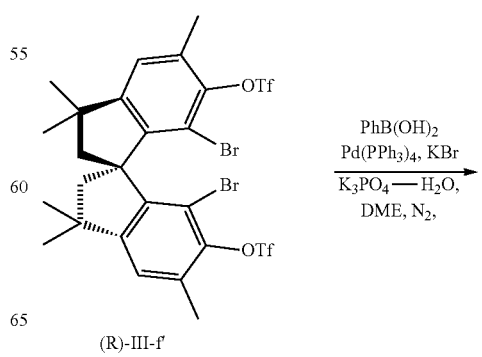

(R)-III-f'

PhB(OH)$_2$
Pd(PPh$_3$)$_4$, KBr
K$_3$PO$_4$—H$_2$O,
DME, N$_2$,
→

-continued

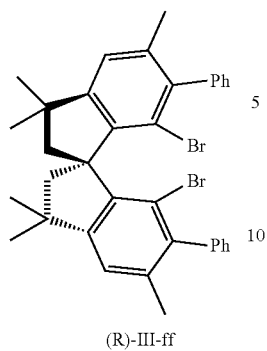

(R)-III-ff

Under nitrogen protection, (R)-III-f (0.22 g), phenylboronic acid 0.3 g, potassium bromide 0.1 g, and tetrakis(triphenylphosphine) palladium (50 mg) were added in a reaction flask, and then 2 mL of glycol dimethyl ether (DME), 1 mL of water and 0.45 g of potassium phosphate tribasic trihydrate were added. The solution reacted under stirring at 90° C. for 24 hours. After the reaction was completed, the reaction was quenched with water, extracted with ethyl acetate, dried over anhydrous sodium sulfate, and suction filtered. The filtrate was concentrated to dryness and purified with the silica gel column flash column chromatography to obtain a powdery solid (R)-III-ff, with a yield of 55%.

Example 9

Synthesis of (R)-3,3,3',3'-tetramethyl-7,7'-diiodo-1,1'-spirobiindane ((R)-III-aa)

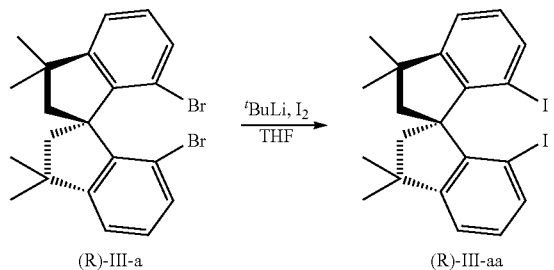

Under nitrogen atmosphere, (R)-III-a (1 g) and 10 mL of anhydrous degassed tetrahydrofuran were added in a flask and cooled to −78° C., and an n-hexane solution of tert-butyllithium (8 mL, 2 mol/L) was added dropwise. The mixture reacted under stirring for 1 hour, then iodine (10 mmol) was added, then the reaction solution was naturally warmed up to room temperature to react overnight, and water was added to quench the reaction. The solution was extracted with ethyl acetate, dried over anhydrous sodium sulfate, and suction filtered. The filtrate was concentrated to dryness and purified with the silica gel column flash column chromatography to obtain (R)-III-aa, with a yield of 80%. $^1$H NMR (400 MHz, CDCl$_3$) δ 7.63 (dd, J=7.7, 0.9 Hz, 2H), 7.19 (dd, J=7.5, 0.9 Hz, 2H), 6.94 (dd, J=14.4, 6.8 Hz, 2H), 2.49 (d, J=13.1 Hz, 2H), 2.27 (d, J=13.0 Hz, 2H), 1.47 (s, 6H), 1.36 (s, 6H).

Example 10

Synthesis of (R)-3,3,5,3',3',5'-hexamethyl-7,7'-bis(diphenylphosphino)-1,1'-spirobiindane ((R)-I-b)

Scheme 1

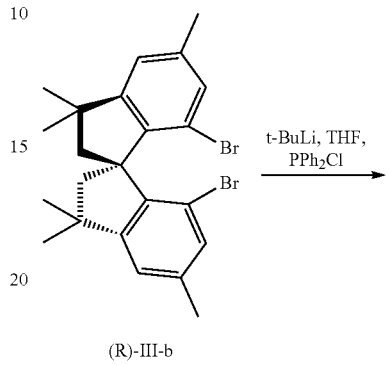

(R)-III-b

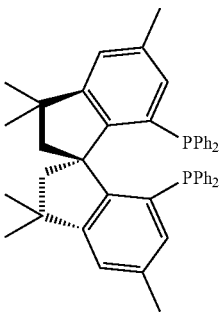

(R)-I-b

Under nitrogen atmosphere, (R)-III-b (1 g, 1.08 mmol) and 15 mL of degassed anhydrous tetrahydrofuran were added in a reaction flask, the temperature was reduced to −78° C., and an n-hexane solution of tert-butyllithium (6 mL, 1.6M) was added. After three hours of reaction, diphenylphosphine chloride (6 mmol) was added. After 30 minutes, the temperature was naturally raised to room temperature, and the reaction continued for 6 hours. After the reaction was completed, the reaction was quenched by adding an appropriate amount of dilute hydrochloric acid. The obtained solution was extracted with ethyl acetate. The organic phase was washed with saturated sodium chloride solution, dried over anhydrous sodium sulfate, and suction filtered. The filtrate was concentrated and purified with silica gel flash column chromatography (eluent: petroleum ether:ethyl acetate=50:1) to obtain a solid (R)-I-b with a yield of 60%, which is the ligand named (R)-HMSDP); melting point: 269-270° C., $[\alpha]_D^{20}$=−96.3° (c 0.12, CH$_2$Cl$_2$); $^1$H NMR (400 MHz, CDCl$_3$): δ=7.23-7.21 (m, 6H), 7.16 (t, J=7.3 Hz, 2H), 7.05-6.98 (m, 10H), 6.85-6.79 (m, 6H), 2.33 (d, J=13.4 Hz, 2H), 2.29 (s, 6H), 2.14 (d, J=13.4 Hz, 2H), 1.25 (s, 6H), 1.15 (s, 6H); $^{31}$P NMR (162 MHz, CDCl$_3$): δ=−20.81 (s); HRMS (EI-TOF): calcd for C$_{47}$H$_{46}$P$_2$ 672.3075, found 672.3079.

Scheme 2

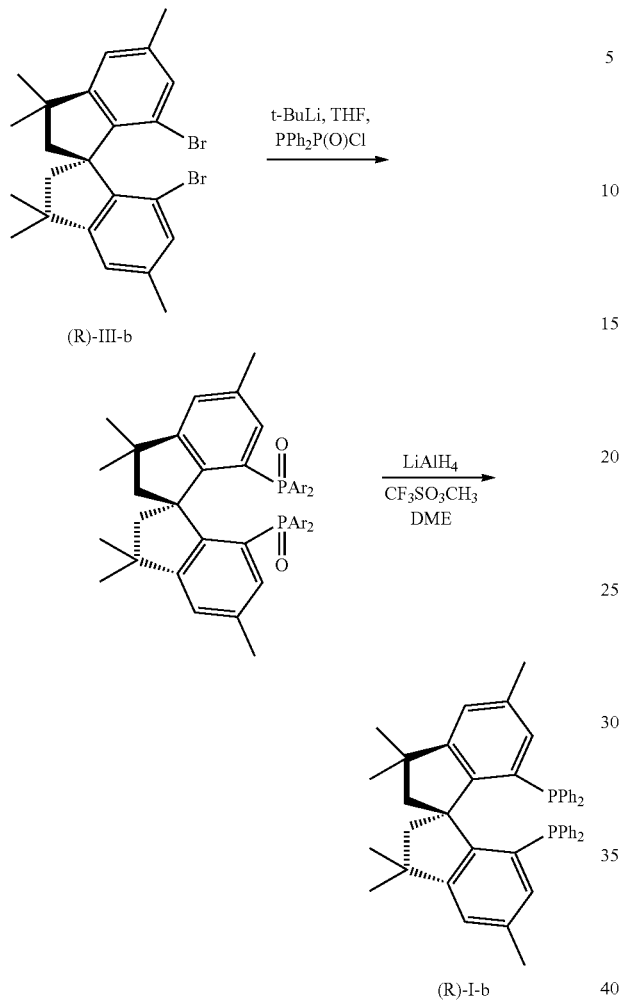

Under nitrogen atmosphere, (R)-III-b (1 g, 1.08 mmol) and 15 mL of degassed anhydrous tetrahydrofuran were added in a flask, the temperature was reduced to −78° C., and an n-hexane solution of tert-butyllithium (4 mL, 1.6M) was added. After three hours of reaction, diphenylphosphinyl chloride (6 mmol) was added. After 30 minutes, the temperature was naturally raised to room temperature, and the reaction continued for 16 hours. After the reaction was completed, the reaction was quenched by adding an appropriate amount of dilute hydrochloric acid. The obtained solution was extracted with ethyl acetate. The organic phase was washed with saturated sodium chloride solution, dried over anhydrous sodium sulfate, and suction filtered. The filtrate was concentrated, and purified with the silica gel flash column chromatography (eluent: petroleum ether:ethyl acetate=2:1) to obtain a white solid hexamethylbis(diphenylphosphinyl) spirobiindane with a yield of 72%. NMR characterization data: $^1$H NMR (400 MHz, CDCl$_3$): δ=7.57-7.48 (m, 4H), 7.43 (td, J=7.3, 1.3 Hz, 2H), 7.35 (ddd, J=8.3, 5.1, 2.1 Hz, 4H), 7.27 (q, J=7.5 Hz, 6H), 7.12 (s, 2H), 7.07 (td, J=7.9, 2.7 Hz, 4H), 6.81 (d, J=14.1 Hz, 2H), 2.43 (d, J=12.8 Hz, 2H), 2.24 (s, 6H), 2.16 (d, J=12.8 Hz, 2H), 1.37 (s, 6H), 1.27 (s, 6H); $^{31}$P NMR (400 MHz, CDCl$_3$): δ=31.22 (s); HRMS (EI-TOF): calcd for C$_{47}$H$_{46}$O$_2$P$_2$ 704.2973, found 704.2977;

Under nitrogen atmosphere, 1 g of hexamethylbis(diphenylphosphinyl) spirobiindane, 12 mL of glycol dimethyl ether, and 0.1 mL of methyl trifluoromethanesulfonate were added in a reaction flask. After stirring at room temperature for 3 hours, the mixture was cooled to 0° C., and 6.6 mL of tetrahydrofuran solution of lithium aluminium hydride (2.5 mol/L) was added to react at 0° C. for about 3 hours, and TLC confirmed that the reaction was finished. The reaction was quenched with dilute hydrochloric acid. The obtained solution was extracted with ether, and washed sequentially with saturated NaHCO$_3$ solution and saturated NaCl. Then the organic phase was dried over anhydrous sodium sulfate, and suction filtered. The filtrate was concentrated and purified with the column chromatography (EA:PE=1:100) to obtain a solid (R)-I-b, with a yield of 90%.

Example 11

Synthesis of (R)-3,3,5,3',3',5'-hexamethyl-7-(diphenylphosphino)-1,1'-spirobiindane ((R)-II-b)

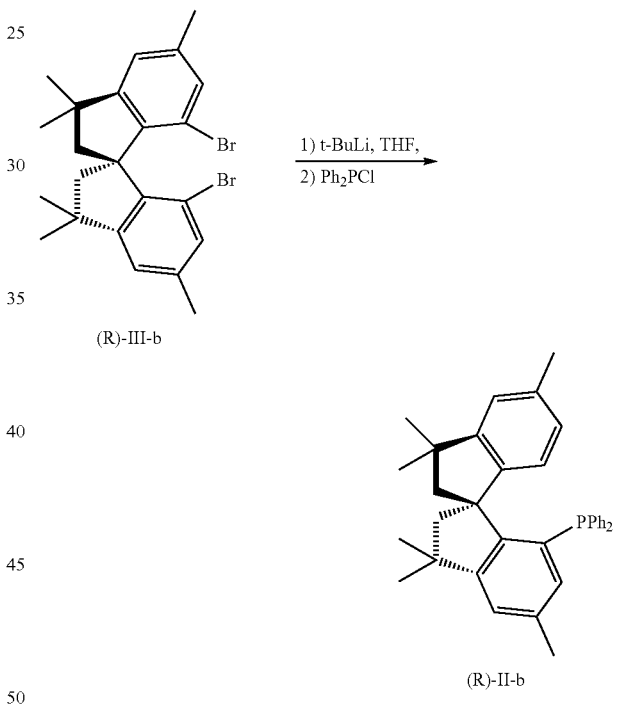

Under nitrogen atmosphere, (R)-III-b (1 g) and 15 mL of degassed anhydrous tetrahydrofuran were added in a reaction flask, the temperature was reduced to −78° C., and an n-hexane solution of tert-butyllithium (6 mL, 1.6M) was added. After three hours of reaction, diphenyl phosphine chloride (1.2 mmol) was added. After 30 minutes, the temperature was naturally raised to room temperature, and the reaction continued for 6 hours. After the reaction was completed, the reaction was quenched by adding an appropriate amount of dilute hydrochloric acid. The obtained solution was extracted with ethyl acetate. The organic phase was washed with saturated sodium chloride solution, dried over anhydrous sodium sulfate, and suction filtered. The filtrate was concentrated and purified with silica gel flash column chromatography (eluent: petroleum ether:ethyl acetate=50:1) to obtain a solid (R)-II-b, with a yield of 66%, melting point: 197-198° C.; $[\alpha]_D^{20}$=5.8° (c 0.06, $CH_2Cl_2$). $^1$H NMR (400 MHz, $CDCl_3$): δ=7.20 (4H), 7.18-7.12 (m, 2H), 7.02 (3H), 6.93-6.87 (m, 3H), 6.78-6.73 (m, 1H), 6.25 (2H), 3.02-2.91 (m, 1H), 2.36 (1H), 2.24 (s, 6H), 2.22 (1H) 2.12 (1H), 1.50 (s, 3H), 1.38 (s, 3H), 1.35 (s, 3H), 1.32 (s, 3H). $^{31}$P NMR (162 MHz, $CDCl_3$): δ=−22.47 (s). $^{13}$C NMR (101 MHz, $CDCl_3$): δ=152.28, 152.20, 151.08, 150.84, 150.76 (d, J=2.9 Hz), 148.07 (d, J=4.1 Hz), 138.64 (d, J=14.7 Hz), 135.69 (t, J=6.7 Hz), 135.04 (d, J=2.8 Hz), 134.79, 132.75, 132.54, 131.98, 131.79, 131.57, 131.36, 130.86 (d, J=9.1 Hz), 126.97, 126.91 (d, J=1.7 Hz), 126.53-126.32 (m), 126.13, 122.73 (d, J=4.2 Hz), 121.02, 59.69, 57.24 (d, J=6.9 Hz), 57.07 (d, J=2.7 Hz), 42.56, 41.89, 31.86 (d, J=2.7 Hz), 31.18, 29.16, 27.35 (d, J=2.6 Hz), 20.30 (d, J=11.9 Hz). HRMS (EI-TOF): calcd for $C_{35}H_{37}P$ 488.2633, found 488.2639.

Example 12

Synthesis of (R)-3,3,5,3',3',5'-hexamethyl-7,7'-bis(bis(4-trifluoromethylphenyl)phosphino)-1,1'-spiro-biindane ((R)-I-bg)

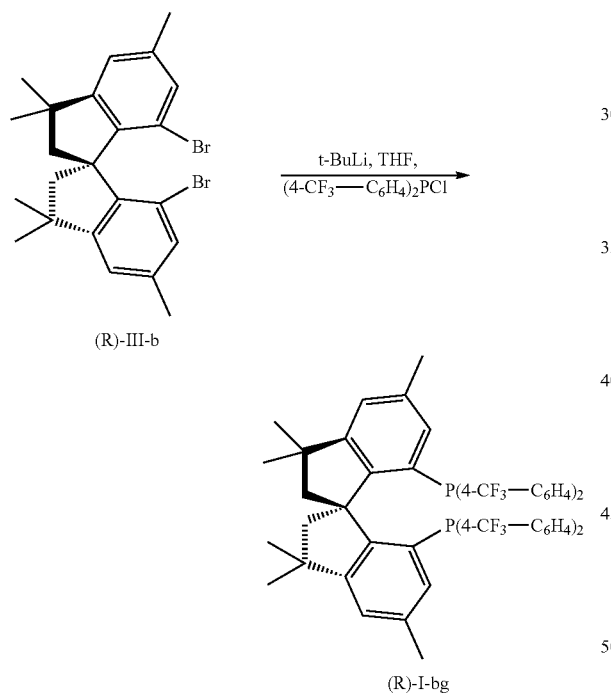

Under nitrogen atmosphere, in a reaction flask, (R)-III-b (1 g, 1.08 mmol) was added and 15 mL of degassed anhydrous tetrahydrofuran was added. The temperature was reduced to −78° C., and an n-hexane solution of tert-butyllithium (6 mL, 1.6M) was added. After three hours of reaction, bis(4-trifluoromethylphenyl) phosphine chloride (6 mmol) was added. After 30 minutes, the temperature was naturally raised to room temperature, and the reaction continued for 6 hours. After completion of the reaction, the reaction was quenched by adding an appropriate amount of dilute hydrochloric acid. The obtained solution was extracted with ethyl acetate. The organic phase was washed with saturated sodium chloride solution, dried over anhydrous sodium sulfate, and suction filtered. The filtrate was concentrated and purified with the silica gel flash column chromatography (eluent: petroleum ether:ethyl acetate=50:1) to obtain a solid (R)-I-bg, with a yield of 55%; $[\alpha]_D^{20}$=120.4° (c 0.07, $CH_2Cl_2$). $^1$H NMR (400 MHz, $CDCl_3$): δ=7.47 (d, J=7.8 Hz, 4H), 7.22 (d, J=7.7 Hz, 4H), 7.06 (s, 2H), 7.04-6.96 (m, 4H), 6.81 (t, J=7.3 Hz, 6H), 2.34 (m, 8H), 2.32 (s, 2H), 1.29 (s, 6H), 1.23 (s, 6H). $^{31}$P NMR (162 MHz, $CDCl_3$): δ=−21.54.

Example 13

Synthesis of (R)-3,3,5,3',3',5'-hexamethyl-7,7'-bis(bis(3,5-di(trifluoromethyl)phenyl)phosphino)-1,1'-spirobiindane ((R)-I-bbg)

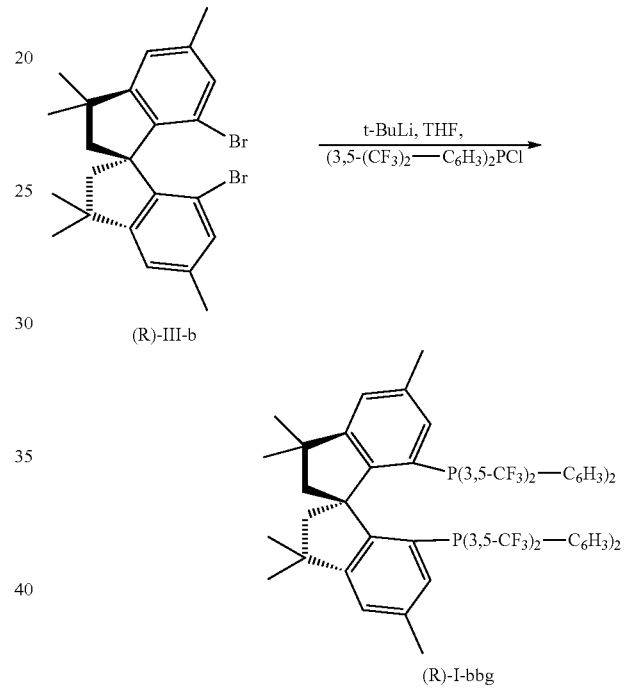

Under nitrogen atmosphere, (R)-III-b (1 g, 1.08 mmol) and 15 mL of degassed anhydrous tetrahydrofuran were added in a reaction flask, and the temperature was reduced to −78° C., and an n-hexane solution of tert-butyllithium (4 mL, 1.6M) was added. After three hours of reaction, bis(3,5-di(trifluoromethyl)phenyl) phosphine chloride (6 mmol) was added. After 30 minutes, the temperature was naturally raised to room temperature, and the reaction continued for 6 hours. After completion of the reaction, the reaction was quenched by adding an appropriate amount of dilute hydrochloric acid. The obtained solution was extracted with ethyl acetate. The organic phase was washed with saturated sodium chloride solution, dried over anhydrous sodium sulfate, and suction filtered. The filtrate was concentrated and purified with the silica gel flash column chromatography (eluent: Petroleum ether:ethyl acetate=40:1) to obtain a solid (R)-I-bbg with a yield of 65%.

Example 14

According to the same reaction process as in Example 13, bis(3,5-di(trifluoromethyl)phenyl)phosphine chloride was replaced with bis(3,4-dimethylphenyl)phosphine chloride, (R)-3,3,5,3',3',5'-hexamethyl-7,7'-bis(bis(3,4-dimethylphenyl)phosphino)-1,1'-spirobiindane ((R)-I-bbb) was obtained with a yield of 73%; melting point: 121-122° C., $[\alpha]_D^{20}=17.9°$ (c 0.11, $CH_2Cl_2$).

Example 15

According to the same reaction process as in Example 13, bis(3,5-bis(trifluoromethyl)phenyl)phosphine chloride was replaced with (4-methoxyphenyl)phosphine chloride, (R)-3,3,5,3',3',5'-hexamethyl-7,7'-bis(bis(4-methoxyphenyl)phosphino)-1,1'-spirobiindane ((R)-1-bbo) was obtained with a yield of 75%.

Example 16

Synthesis of (R)-3,3,3',3'-tetramethyl-7,7'-bis(diphenylphosphino)-1,1'-spirobiindane ((R)-I-a)

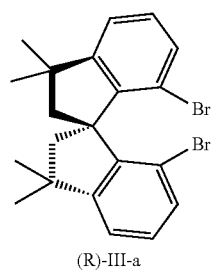

(R)-III-a t-BuLi, THF,
PPh₂Cl
→

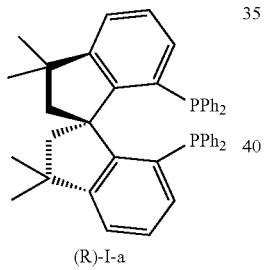

(R)-I-a

Under nitrogen atmosphere, (R)-III-a (1 g) and 15 mL of degassed anhydrous tetrahydrofuran were added in a reaction flask. The temperature was reduced to −78° C., and an n-hexane solution of tert-butyllithium (5 mL, 1.6 M) was added. After three hours of reaction, diphenylphosphine chloride (6 mmol) was added. After 30 minutes, the temperature was naturally raised to room temperature, and the reaction continued for 6 hours. After the reaction was completed, dilute hydrochloric acid was added to quench the reaction. The obtained solution was extracted with ethyl acetate, washed with sodium chloride solution, dried over anhydrous sodium sulfate, and suction filtered. The filtrate was concentrated and purified with the silica gel flash column chromatography (eluent: petroleum ether:ethyl acetate=50:1) to obtain a solid (R)-I-a with a yield of 72%, which is ligand named (R)-MSDP). $^1$H NMR (400 MHz, CDCl₃) δ 7.27 (t, J=7.5 Hz, 2H), 7.23-7.15 (m, 10H), 7.09-7.01 (m, 6H), 7.00-6.94 (m, 4H), 6.79 (t, J=7.1 Hz, 4H), 2.36 (d, J=13.2 Hz, 2H), 2.19 (d, J=13.2 Hz, 2H), 1.27 (s, 6H), 1.17 (s, 6H). HRMS (EI-TOF) for $C_{45}H_{42}P_2$: 644.2764.

Example 20

Synthesis of complex $RuCl_2$-[(R)-HMSDP] [(R,R)-DPEN]

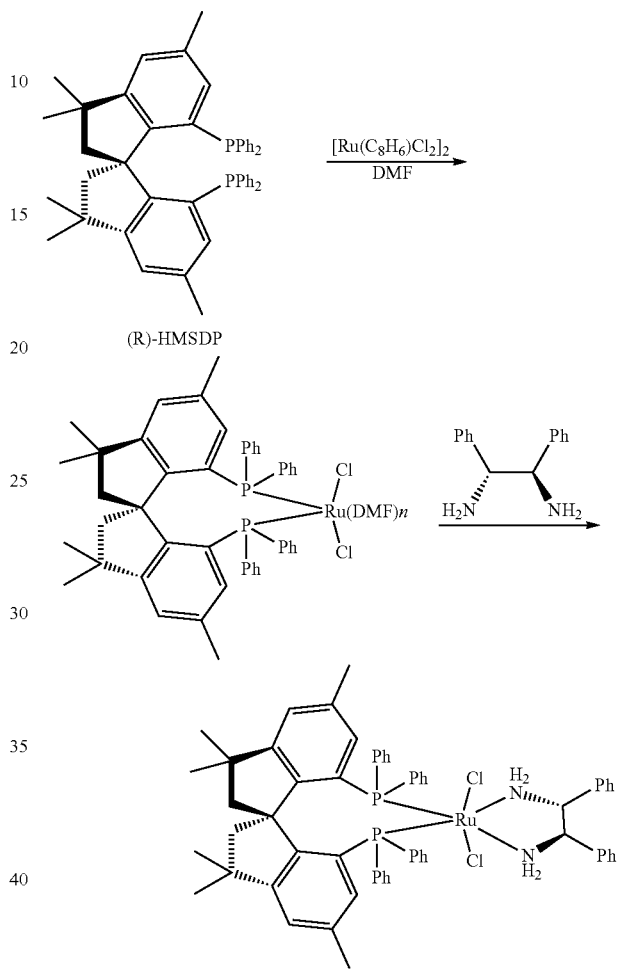

In a glove box having nitrogen atmosphere, methyl spirophosphine ligand (R)-HMSDP (0.165 mmol, i.e., compound (R)-I-b) and $Ru(C_6H_6)Cl_2$ (0.08 mmol, 40 mg) were weighed and added to a Schlenk reaction tube. 3 mL of dry and degassed N, N-dimethylformamide (DMF) was then injected under nitrogen atmosphere, heated to 100° C. under stirring for 2 hours, then cooled to room temperature, and added with (R, R)-1, 2-diphenylethylenediamine ((R, R)-DPEN, 0.165 mmol, 35 mg). The reaction continued under stirring at room temperature for 16 hours. The solvent was removed under vacuum, and after drying, a quantitative solid product $RuCl_2$-[(R)-HMSDP] [(R, R)-DPEN] was obtained.

Example 21

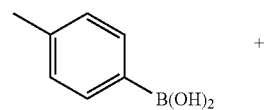

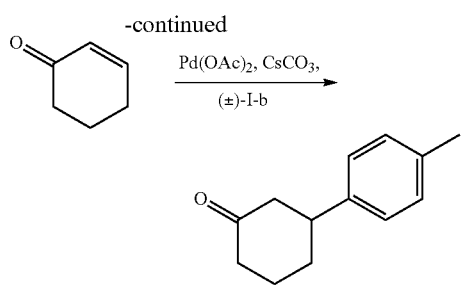

Under nitrogen atmosphere, 0.4 g of p-tolylboronic acid, 0.2 g of cyclohexenone, 23 mg of palladium acetate, 0.6 g of cesium carbonate, and 83 mg of methyl spiro phosphine ligand (±)-1-b (raceme) were added in a reaction flask, and then 8 ml of toluene and 30 μl of chloroform were injected. The mixture reacted under stirring at 80° C. for 48 hours. The reaction solution was washed with saturated brine. The organic phase was dried over sodium sulfate and then purified with the column chromatography to obtain 330 mg of product 3-(p-tolyl)-cyclohexanone, with a yield of 85%. $^1$H NMR (400 MHz, CDCl$_3$) δ=7.20-7.03 (m, 4H), 2.98 (m, 1H), 2.57 (m, 1H), 2.52 (m, 1H), 2.49-2.42 (m, 1H), 2.42-2.35 (m, 1H), 2.33 (s, 3H), 2.18-2.10 (m, 1H), 2.06 (m, 1H), 1.89-1.70 (m, 2H).

Example 22

Under nitrogen atmosphere, 4.8 mg of chiral methyl spiro phosphine ligand (S)-HMSDP and 1 mg of metal [Pd(C$_3$H$_5$)Cl]$_2$) were weighed and added into a Schlenk reaction tube, and 1 mL of toluene was added. The mixture was stirred for 2 hours at room temperature, then cooled to −25° C., and added with 32 mg of 1,3-bis (o-chlorophenyl)-2-allyl acetate. Then, a mixture of dibenzyl malonate (45 μl), Et$_2$Zn (300 μl, IM in hexane) and 1 mL of toluene solution, which were previously mixed and stirred for 30 minutes, was added, and the obtained solution was incubated at −25° C. for 2 hours. Then, the reaction was quenched by adding a saturated ammonium chloride solution, and the obtained solution was extracted with ethyl acetate. The organic phase was washed with a saturated sodium chloride solution, dried over anhydrous sodium sulfate to remove the solvent, and then purified with the silica gel column chromatography (ethyl acetate:petroleum ether=1:20)) to obtain a chiral allylated target product, with a yield of 90%, ee=88%; HPLC conditions: Chiralcel IA, $^i$PrOH:Hexane=85:15, flow rate 1.0 mL/min, room temperature, 254 nm, t$_1$: 9.66 min (minor product), t$_2$: 11.88 min (main product). $^1$H NMR (400 MHz, CDCl$_3$) δ=7.39-7.27 (m, 1H), 7.27-7.20 (m, 10H), 7.20-7.08 (m, 7H), 6.84 (d, J=15.8 Hz, 1H), 6.29 (m, 1H), 5.13 (d, J=1.0 Hz, 2H), 4.98 (q, J=12.3 Hz, 2H), 4.89 (t, J=9.6 Hz, 1H), 4.24 (d, J=10.5 Hz, 1H).

Example 23

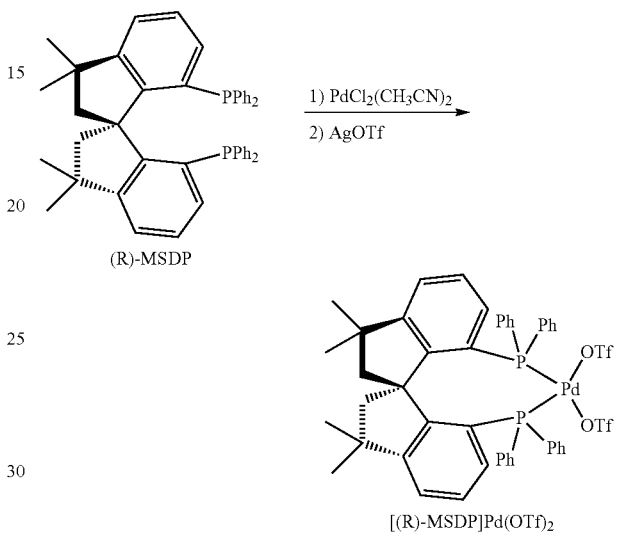

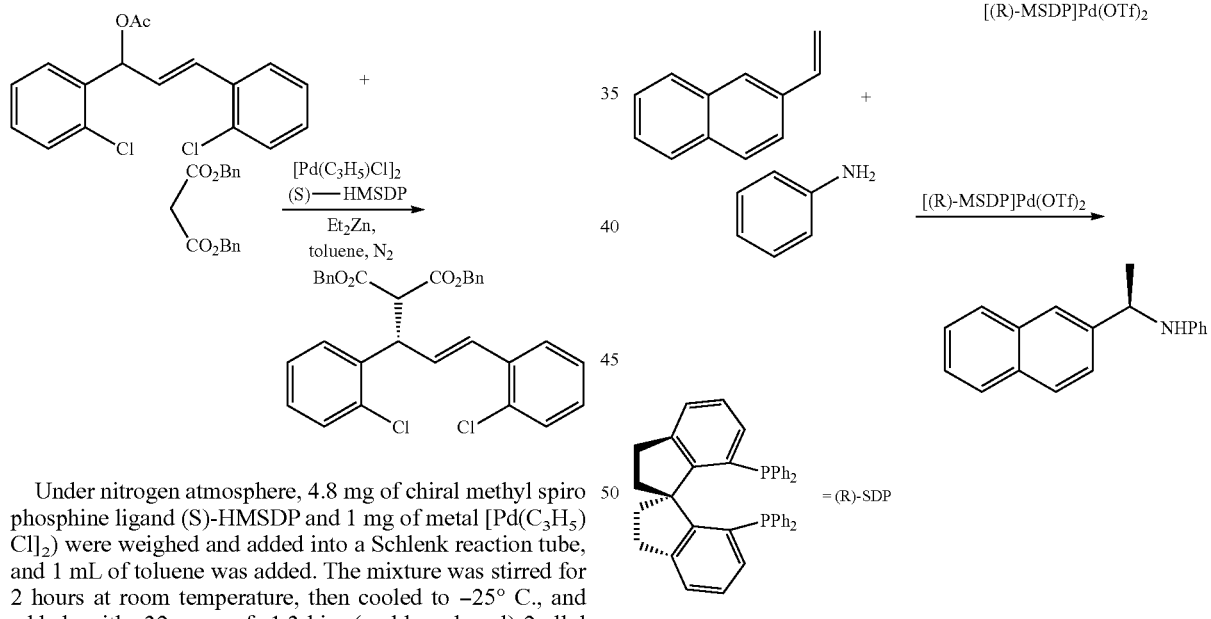

Under nitrogen atmosphere, bis(acetonitrile)dichloropalladium(II) (26 mg, 0.1 mmol) and (R)-MSDP (0.1 mmol) were weighed and mixed in 2 mL of toluene. The mixture reacted under stirring for 2 hours, and was evaporated under reduced pressure to remove the solvent and to be dried. 6 mL of dichloromethane was added, then 3 mL of acetonitrile containing silver trifluoromethanesulfonate (51 mg, 0.2 mmol) was added. The reaction continued under stirring for 5 minutes. The obtained solution was filtered with suction. The filter cake was washed with dichloromethane, the filtrate was concentrated and dried under high vacuum to obtain [(R)-MSDP]Pd(OTf)$_2$ in a quantitative yield. Under nitrogen atmosphere, 0.01 mmol of catalyst [(R)-MSDP]Pd(OTf)$_2$, 0.5 mmol of freshly distilled aniline and 0.75 mmol of 2-naphthyl ethylene were added in a reaction flask, 1 mL of anhydrous, degassed toluene was injected, and then the reaction was conducted under stirring at 75° C. for 40 hours to end the reaction. Purification was performed with the silica gel column chromatography (ethyl acetate:petroleum ether=1:35) to obtain a target product of asymmetric hydroamination reaction, with a yield of 61%, 41% ee. HPLC conditions: Chiralpak OD-H, n-hexane/EtOH=98/2, flow rate: 0.8 mL/min, room temperature, 254 nm, t$_1$: 20.8 min (main product), t$_2$: 22.8 min (minor product). $^1$H NMR (400 MHz, CDCl$_3$) δ 7.79 (dd, J=10.9, 5.5 Hz, 4H), 7.53-7.39 (m, 3H), 7.12-7.03 (m, 2H), 6.63 (t, J=7.3 Hz, 1H), 6.59-6.51 (m, 2H), 4.63 (q, J=6.7 Hz, 1H), 4.11 (s, 1H), 1.58 (d, J=6.7 Hz, 3H).

As a comparison, according to the above process, (R)-MSDP was replaced with (R)-SDP, the obtained target product of asymmetric hydroamination reaction had a yield of 10%, 0% ee. That is, the product was raceme.

Example 24

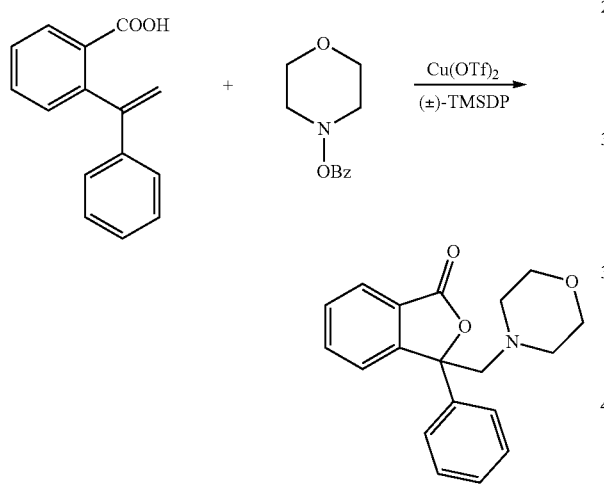

Under nitrogen atmosphere, 0.05 mmol copper trifluoromethanesulfonate and 0.06 mmol (±)-TMSDP were added in a reaction flask, and 1 mL of 1, 2-dichloroethane was injected. The mixture was stirred at room temperature for 30 minutes, and then 0.5 mmol of 2-(1-styryl) benzoic acid and 1 mmol morpholine benzoate were added to reflux for 1 hour. The reaction solution was added with dichloroethane, washed with saturated sodium bicarbonate, and washed with saturated brine. The organic phase was dried over anhydrous sodium sulfate, then concentrated, and purified by the silica gel column chromatography (ethyl acetate:petroleum ether=1:2) to obtain a target product of a cyclization reaction, with a yield of 81%. $^1$H NMR (CDCl3, 400 MHz): δ 7.91 (d, J=7.6 Hz, 1H), 7.66-7.49 (m, 5H), 7.41-7.29 (m, 3H), 3.48-3.40 (m, 2H), 3.38-3.29 (m, 2H), 3.21 (d, J=14.2 Hz, 1H), 3.14 (d, J=14.2 Hz, 1H), 2.60-2.50 (m, 2H), 2.27-2.17 (m, 2H).

Example 25

Under nitrogen atmosphere, (R)-III-b (1 mmol) and 5 mL of ethanol were added in a reaction flask to be dissolved under stirring and refluxing. The solution was then added slowly to 3 mL of ethanol solution in which HAuCl$_4$.4H$_2$O (206 mg, 0.5 mmol) was dissolved, and then reacted under stirring at room temperature for 2 hours, followed by performing suction filtration. The filter cake was dissolved in 5 mL of dichloromethane, and then 50 mL of petroleum ether was added to precipitate a precipitate. Then, the suction filtration was performed, and the filter cake was dried under vacuum to obtain a complex compound of monovalent gold salt, [(R)-III-b]AuCl, with a yield of 80%.

Example 26

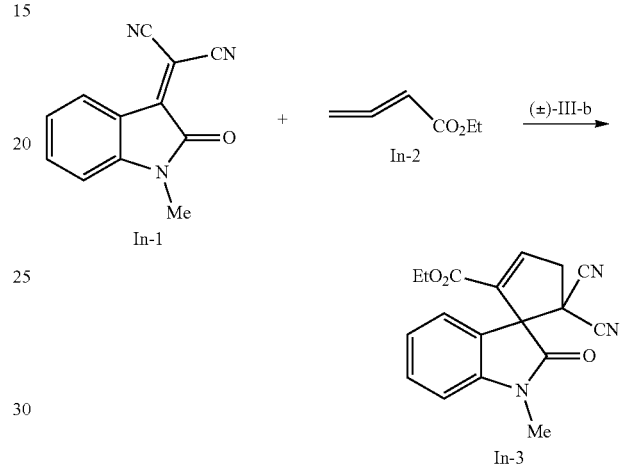

Under nitrogen atmosphere, III-b (0.05 mmol), 0.5 mmol ethyl allenyl formate (In-2) and olefin In-1 were added in a reaction flask, and then 5 mL of toluene was added. The mixture was stirred at room temperature for 12 hours. The reaction solution was concentrated, and then purified silica gel column chromatography to obtain a product In-3 of [3+2]cyclization product, with a yield of 80%.

By performing the above reaction with racemic MSDP instead of III-b, a product In-3 of [3+2] cyclization product can be obtained with a yield of 71%.

What is claimed is:

1. A 3,3,3',3'-tetramethyl-1,1'-spirobiindane-based phosphine ligand, being a compound represented by formula I or formula II, or being an enantiomer, a raceme or a diastereomer thereof:

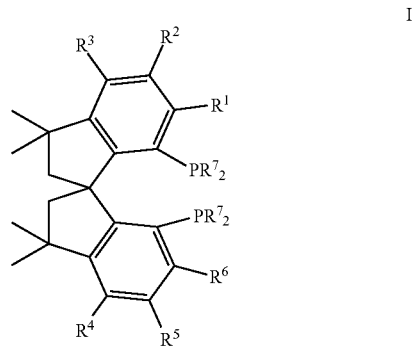

I

-continued

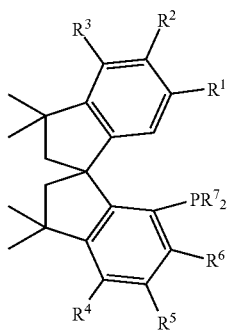
II wherein $R^1$ and $R^6$ are each independently selected from the group consisting of hydrogen, $C_1$-$C_{10}$ alkyl or perfluoroalkyl, $C_3$-$C_6$ cycloalkyl, and $C_1$-$C_4$ alkoxy or perfluoroalkoxy; $R^2$, $R^3$, $R^4$, and $R^5$ are each independently selected from the group consisting of hydrogen, halogen, $C_1$-$C_{10}$ alkyl or perfluoroalkyl, $C_3$-$C_6$ cycloalkyl, and $C_1$-$C_4$ alkoxy or perfluoroalkoxy; and $R^7$ is selected from the group consisting of $C_1$-$C_{10}$ alkyl or perfluoroalkyl, $C_3$-$C_6$ cycloalkyl, and $C_6$-$C_{14}$ aryl.

2. A synthesis method of the compound represented by formula I according to claim 1, wherein a racemic or optically active compound represented by formula III, as a raw material, reacts with a di-substituted phosphine halide under an effect of an alkali to obtain the compound represented by formula I via a double-substitution reaction in accordance with the following reaction equation:

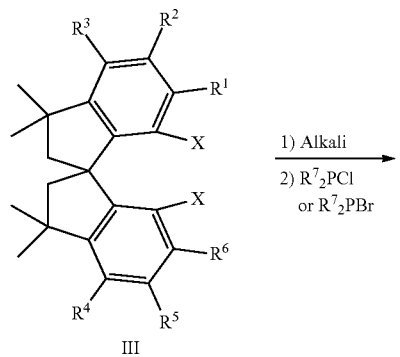

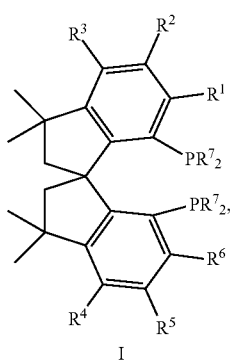
I or wherein the compound represented by formula III and a di-substituted phosphine oxyhalide are subjected to a double-substitution reaction under an effect of an alkali to prepare a compound represented by formula 6, which is then subjected to a reduction reaction to prepare the compound represented by formula I, in accordance with the following reaction equation:

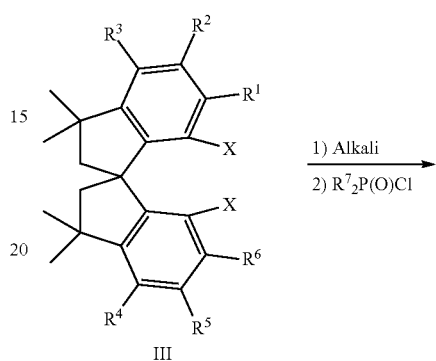

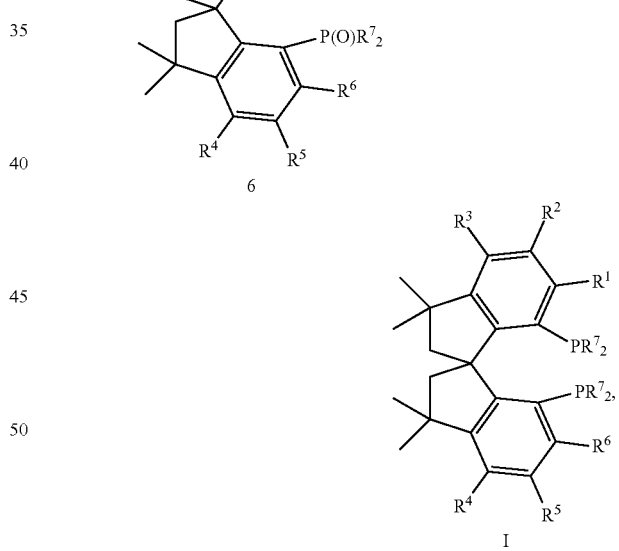

and wherein X is halogen, and $R^1$-$R^7$ are the same as those defined in claim 1.

3. A synthesis method of the compound represented by formula II according to claim 1, wherein a racemic or optically active compound represented by formula III, as a raw material, reacts with di-substituted phosphine halide under an effect of an under alkali to obtain the compound represented by the formula II via a mono-substitution reaction in accordance with the following reaction equation:

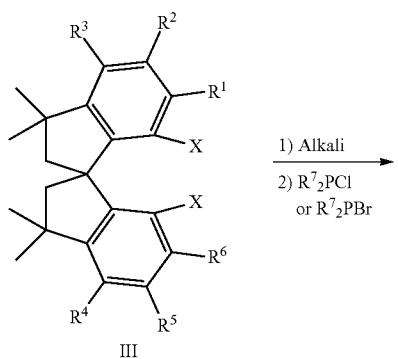

III

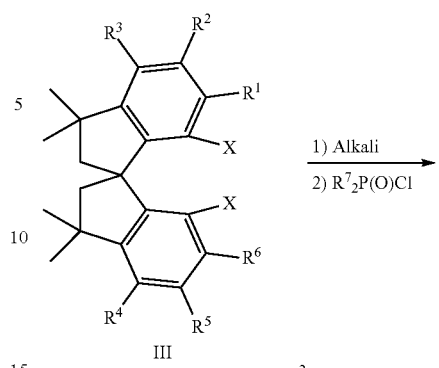

III

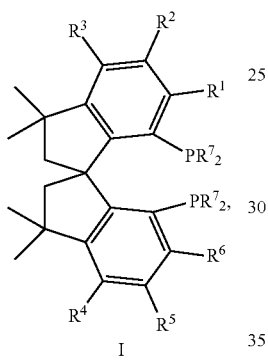

I or wherein the compound represented by formula III and di-substituted phosphine oxyhalide are subjected to a mono-substitution reaction under an effect of an alkali to prepare a compound represented by formula 7, which is then subjected to a reduction reaction to prepare the compound represented by formula II, in accordance with the following reaction equation:

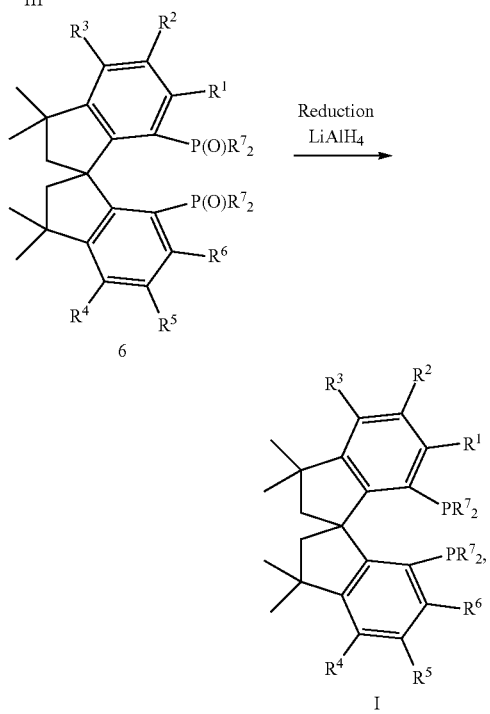

and wherein X is halogen, and $R^1$-$R^7$ are the same as those defined in claim 1.

* * * * *